US009458160B2

(12) United States Patent
Maitra et al.

(10) Patent No.: US 9,458,160 B2
(45) Date of Patent: *Oct. 4, 2016

(54) PERIPHERALLY RESTRICTED DIPHENYL PURINE DERIVATIVES

(71) Applicant: RESEARCH TRIANGLE INSTITUTE, Research Triangle Park, NC (US)

(72) Inventors: Rangan Maitra, Cary, NC (US); Alan Bradley Fulp, Willow Spring, NC (US); Yanan Zhang, Apex, NC (US); Herbert H. Seltzman, Raleigh, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/922,583

(22) Filed: Oct. 26, 2015

(65) Prior Publication Data

US 2016/0046630 A1 Feb. 18, 2016

Related U.S. Application Data

(63) Continuation of application No. 14/378,479, filed as application No. PCT/US2013/026359 on Feb. 15, 2013, now Pat. No. 9,187,480.

(60) Provisional application No. 61/600,229, filed on Feb. 15, 2013, provisional application No. 61/699,523, filed on Sep. 11, 2012.

(51) Int. Cl.
*C07D 401/04* (2006.01)
*C07D 473/32* (2006.01)
*C07D 473/34* (2006.01)

(52) U.S. Cl.
CPC .................. *C07D 473/34* (2013.01)

(58) Field of Classification Search
CPC . C07D 401/04; C07D 473/32; C07D 473/34
See application file for complete search history.

(56) References Cited

U.S. PATENT DOCUMENTS 6,579,868 B1    6/2003  Asano et al.
2008/0097097 A1  4/2008  Ragan
2014/0107157 A1  4/2014  Fulp et al.

FOREIGN PATENT DOCUMENTS

WO    WO 2004/037823    5/2004
WO    WO 2010/019762    2/2010

OTHER PUBLICATIONS

Fulp et al., "Diphenyl Purine Derivatives as Peripherally Selective Cannabinoid Receptor 1 Antagonists," *Journal of Medicinal Chemistry*, 2012, pp. 10022-10032, vol. 55, No. 2.
Griffith et al., "Discovery of 1-[9-(4-Chlorophenyl)-8-(2-chlorophenyl)-9H-purin-6-yl]-4-ethylaminopiperidine-4-carboxylic Acid Amide Hydrochloride (CP-945,598), a Novel, Potent, and Selective Cannabinoid Type 1 Receptor Antagonist," *J. Med. Chem.* 2009, vol. 52, pp. 234-237.
Ragan et al., "Development of a Practical and Efficient Synthesis of CP-945,598-01, a $CB_1$ Antagonist for the Treatment of Obesity," *Organic Process Research & Development*, 2009, vol. 13, pp. 186-197.

*Primary Examiner* — Bruck Kifle
(74) *Attorney, Agent, or Firm* — Womble Carlyle Sandridge & Rice, LLP

(57) ABSTRACT

The invention provides compounds capable of acting as antagonists at cannabanoid receptors according to the following formula:

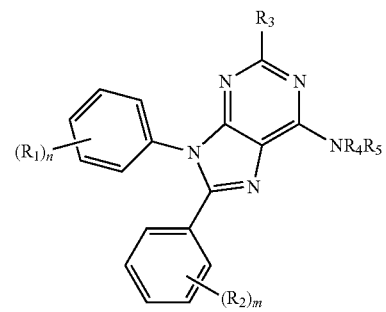

Such compounds may be used to treat conditions for which the cannabinoid receptor system has been implicated, such as obesity, liver disease, diabetes, pain, and inflammation.

20 Claims, No Drawings

PERIPHERALLY RESTRICTED DIPHENYL PURINE DERIVATIVES

CROSS-REFERENCE TO RELATED APPLICATIONS

The present application is a continuation of U.S. application Ser. No. 14/378,479, which is a U.S. National Stage of International Patent Application PCT/US2013/026359, filed Feb. 15, 2013, which claims priority to U.S. Provisional Application No. 61/600,229, filed Feb. 17, 2012 and U.S. Provisional Patent Application No. 61/699,523, filed Sep. 11, 2012. The disclosures of each of the applications noted above are incorporated herein by reference in their entirety.

FEDERALLY SPONSORED RESEARCH OR DEVELOPMENT

This invention was made with United States Government support under Research Grants IR21AA019740-01 and IR03AA017514-01, awarded by the National Institutes of Health's National Institute on Alcohol Abuse and Alcoholism. The United States Government has certain rights in the invention.

FIELD OF THE INVENTION

The present application is directed to various compounds and methods of preparation of compounds that are capable of functioning as cannabinoid receptor 1 (CB1) antagonists. The application is also directed to pharmaceutical compositions containing one or more of these compounds, which may also contain one or more additional therapeutic agents. It is also directed to methods of treatment of various conditions that may be responsive to antagonism of the CB1 receptors, including, but not limited to, metabolic syndromes (including liver disease, obesity, and diabetes).

BACKGROUND OF THE INVENTION

Cannabinoid receptors (CBRs) belong to the endocannabinoid (EC) system, which consists of receptors, transporters, endocannabinoids, and enzymes involved in synthesis and degradation of endocannabinoids. The EC system regulates many important physiological processes and several components of the EC system are under evaluation as targets to treat a diverse array of indications including obesity, liver disease, diabetes, pain and inflammation. To date, two different cannabinoid receptors have been identified (referred to as CB1 and CB2). CB1 and CB2 receptors fall within the class of G protein-coupled receptors, and primarily function to activate inhibitory G proteins (Gi/o).

The CB1 receptor is prominently expressed in the central nervous system (CNS) and also in peripheral tissues. Accordingly, drugs tarteting the CB1 receptors have been developed over the years to treat various metabolic disorders including obesity and diabetes. The first drug selective for CB1 that was developed for medical use was rimonabant, an inverse agonist/antagonist. Rimonabant was designed to treat obesity and other related disorders that have both CNS and peripheral components. Although rimonabant has demonstrated clinical efficacy in clinical trials, it was withdrawn from European markets and denied FDA approval in the United States due to CNS-related side effects including anxiety, depression and suicidal ideation. The development of other related compounds (e.g., taranabant, otenabant, and ibipinabant) was discontinued based on these noted side effects. Accordingly, it would be beneficial to provide CB1 antagonists that are effective, but that do not result in such CNS-related side effects.

SUMMARY OF THE INVENTION

The present invention provides compounds useful as antagonists of the CB1 receptor and methods of synthesis of such compounds. In certain embodiments, peripherally restricted compounds that do not cross the blood-brain barrier have been developed in an effort to maintain the ability to block the CB1 receptor while minimizing CNS-related side effects.

It also provides pharmaceutical compositions containing the compounds, which may be useful in the treatment of various conditions and/or disorders responsive to the antagonism of CB1 receptors. The invention further provides methods of treating such conditions and/or disorders, including but not limited to, metabolic disorders/syndromes including liver disease, obesity, diabetes, and dyslipidemias. For example, in one aspect, the present invention is directed to a method of treating a condition comprising administering to a subject in need of treatment of the condition a pharmaceutical composition comprising a therapeutically effective amount of a compound of the present invention or a pharmaceutically acceptable ester, amide, salt, solvate, prodrug, or isomer thereof.

Accordingly, in one aspect, the present invention provides a compound that acts as an antagonist at CB1 receptors. In some embodiments, the invention provides a compound according to Formula I:

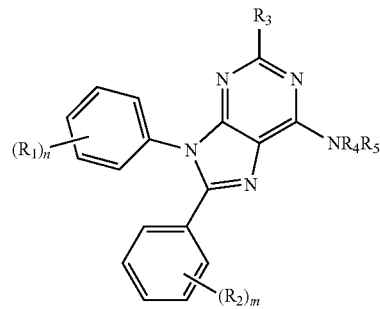

Formula I wherein:
each $R_1$, $R_2$, and $R_3$ is H or a substituent independently selected from the group consisting of halo, OH, optionally substituted C1-10 alkyl (e.g., $CF_3$), optionally substituted C1-10 alkoxy, optionally substituted C2-4 alkenyl, optionally substituted C2-4 alkynyl, $NR_6R_7$, $NR_6COR_7$, $NR_6CO_2R_7$, $CR_6R_7OR_8$, $CONR_6R_7$, $CO_2R_6$, CN, $NO_2$, $N_3$, C1-3 alkylthio, $R_9SO$, $R_9SO_2$, $CF_3S$, and $CF_3SO_2$;
$R_4$ is H or C1-10 alkyl;
$R_5$ is:

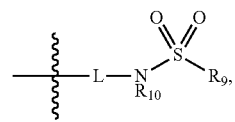

or an optionally substituted piperidine ring, connected through a carbon atom;

or $R_4$ and $R_5$ taken together form a piperidine ring with the nitrogen atom to which they are attached, wherein the piperidine ring is substituted with a substituent selected from the group consisting of $NR_6SO_2R_9$, $NR_6CONR_7R_{11}$, $NR_6COR_{15}$, and $NR_6CO_2R_7$ and is optionally further substituted with one or more substituents independently selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, and $CF_3SO_2$, $NR_6SO_2R_9$, $NR_6CONR_7R_{11}$, $NR_6CO_2R_7$, and $CONR_6R_7$;

or $R_4$ and $R_5$ taken together form an optionally substituted thiomorpholine 1,1-dioxide ring;

$R_6$, $R_7$, and $R_8$ are independently selected from H and optionally substituted C1-10 alkyl;

$R_9$ is H, optionally substituted C1-10 alkyl (e.g., $CF_3$), $NR_6R_7$, or $NR_6COR_7$;

$R_{10}$ is H or optionally substituted C1-10 alkyl;

$R_{11}$ is selected from the group consisting of H, optionally substituted C1-10 alkyl, and $CR_6R_7CO_2R_8$;

$R_{15}$ is optionally substituted C1-12 alkyl, optionally substituted C1-12 heteroalkyl, optionally substituted C1-6alkyl(amino), or optionally substituted aryl;

L is a linker comprising an optionally substituted C1-15 alkyl or C1-15 heteroalkyl;

m and n are each independently integers from 0 to 5;

or a pharmaceutically acceptable ester, amide, salt, solvate, prodrug, or isomer thereof.

In certain embodiments, n is 1 and the $R_1$ substituent is at the para position and m is 1 and the $R_2$ substituent is at the ortho position. In some embodiments, $R_1$ and $R_2$ are both halo substituents (e.g., Cl). In certain embodiments, $R_3$ is H. In some embodiments, $R_4$ is H.

In some embodiments, the alkyl or heteroalkyl of L can comprise one or more cycloalkyl (e.g., cyclohexyl) or cycloheteroalkyl (e.g., piperidine) rings. For example, the alkyl or heteroalkyl group may comprise an optionally substituted cyclohexyl group. For example, L can be $CH_2$—$C_6H_{10}$—$CH_2$. In certain embodiments, $R_{10}$ is H. In certain embodiments, $R_9$ is selected from $CH_3$ and $NH_2$.

In certain embodiments, $R_4$ and $R_5$ taken together form a piperidine ring with the nitrogen atom to which they are attached. In certain embodiments, the piperidine ring is substituted at the 4 position with one or two substituents and may be optionally substituted at other positions on the piperdine ring. In certain embodiments, the piperidine is disubstituted at the 4 position, wherein one piperidine substituent at the 4 position is an optionally substituted aryl (e.g., phenyl) group and the other piperidine substituent at the 4 position is selected from the group consisting of $NR_6SO_2R_9$, $NR_6CONR_7R_{11}$, $NR_6COR_{15}$, and $NR_6CO_2R_7$. In certain embodiments, $R_6$ is H. In some embodiments, $R_9$ is $CH_3$. In certain embodiments, one piperidine substituent (e.g., at the 4 position) is a sulfamide or sulfonamide, $NR_6SO_2R_9$ (e.g., $NHSO_2CH_3$). In certain embodiments, one piperidine substituent (e.g., at the 4 position) is a carbamate, $NR_6CO_2R_7$ (e.g., NHC(O)O-t-butyl). In certain embodiments, one piperidine substituent (e.g., at the 4 position) is an amide, $NR_6CO_2R_{15}$. In certain embodiments, $R_{15}$ can comprise an alkyl (including one or more cycloalkyl groups). In certain embodiments, one piperidine substituent (e.g., at the 4 position) is a urea, $NR_6CONR_7R_8$. In some exemplary urea substituents, $R_6$ and $R_7$=H. In certain urea substituents, $R_{11}$ is an alkyl, selected from the group consisting of ethyl, propyl (n-propyl and isopropyl), butyl (n-butyl, sec-butyl, isobutyl, or t-butyl). In some embodiments, the $R_{11}$ alkyl may comprise one or more cycloalkyl (e.g., cyclohexyl) rings. In some embodiments, $R_{15}$ may comprise one or more cycloalkyl (e.g., cyclohexyl) rings.

In certain embodiments, the compounds of the invention comprise one or more chiral centers. In some embodiments, the compounds may be provided in an enantiomeric or racemic form.

In another aspect of the invention is provided a method for treating or delaying the progression of disorders that are alleviated by antagonizing the CB1 receptor, the method comprising administering a compound as disclosed herein. The disorder can be any disorder that is responsive to antagonism of the CB1 receptor. For example, in certain embodiments, the disorder is selected from the group consisting of obesity, liver diseases, diabetes, pain, inflammation, and dyslipidemia.

In another aspect, a pharmaceutical composition is provided, comprising any of the compounds disclosed herein and one or more pharmaceutically acceptable carriers.

DETAILED DESCRIPTION OF THE INVENTION

The present invention now will be described more fully hereinafter. However, the invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The present invention provides compounds that may function as antagonists at the CB1 receptor, as well as methods of preparation and pharmaceutical compositions thereof. In some specific embodiments, the invention provides compounds that are peripherally selective CB1 antagonists. It also provides methods for using such compounds to treat a variety of disorders that may be responsive to the antagonism of CB1 receptors. In particular, the compositions and methods can be used in the treatment of obesity. Treatment can comprise the use of a compound of the present invention as a single active agent. In other embodiments, treatment can comprise the use of a compound of the present invention in combination with one or more further active agents. The specific pharmaceutical composition (or compositions) used in the invention, and the methods of treatment provided by the invention, are further described below.

Definitions

The term "alkyl" as used herein means saturated straight, branched, or cyclic hydrocarbon groups (i.e., cycloalkyl groups). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "heteroalkyl" as used herein means an alkyl group, having at least one atom within the chain which is not carbon. Preferred heteroatoms include sulfur, oxygen, and nitrogen.

"Optionally substituted" in reference to a substitutent group refers to substituent groups optionally substituted with one or more moieties selected from the group consisting of, for example, halo (e.g., Cl, F, Br, and I); alkyl (e.g., C1-10 alkyl), halogenated alkyl (e.g., $CF_3$, 2-Br-ethyl, $CH_2F$, $CH_2Cl$, $CH_2CF_3$, or $CF_2CF_3$); C2-4 alkenyl, C2-4 alkynyl; hydroxyl; amino; amido; carboxylate; carboxamido; carbamate; carbonate; urea; acetate; alkylamino; arylamino; C1-10 alkoxy; aryl; aralkyl; aryloxy; nitro; azido; cyano; thio; alkylthio; sulfonate; sulfide; sulfinyl; sulfo; sulfate; sulfoxide; sulfamide; sulfonamide; phosphonic acid; phosphate; and/or phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "halo" or "halogen" as used herein means fluorine, chlorine, bromine, or iodine.

The term "alkylthio" as used herein means a thio group with one or more alkyl substituents, where alkyl is defined as above.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined below.

The term "amino" as used herein means a moiety represented by the structure $NR_2$, and includes primary amines, and secondary and tertiary amines substituted by alkyl or aryl (i.e., alkylamino or arylamino, respectively). Thus, $R_2$ may represent two hydrogen atoms, two alkyl moieties, two aryl moieties, one aryl moiety and one alkyl moiety, one hydrogen atom and one alkyl moiety, or one hydrogen atom and one aryl moiety.

Alkyl(amino) is a moiety represented by the structure —$RNR_2$ and includes an alkyl group as defined above attached to an amino group as defined above, wherein the moiety is attached to another portion of a molecule via the alkyl group.

The tem "cycloalkyl" means a non-aromatic, monocyclic or polycyclic ring comprising carbon and hydrogen atoms.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

Active Agents

The present invention provides compounds, methods of preparation of the compounds, pharmaceutical compositions, and methods of treatment of various conditions using such compounds and pharmaceutical compositions.

In some embodiments, compounds according to the following structure are provided:

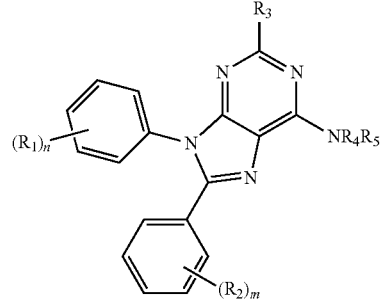

Formula I wherein:
each $R_1$, $R_2$, and $R_3$ is H or a substituent independently selected from the group consisting of halo (e.g., Cl, F, or Br), OH, optionally substituted C1-10 alkyl, optionally substituted C1-10 alkoxy, optionally substituted C2-4 alkenyl, optionally substituted C2-4 alkynyl, $NR_6R_7$, $NR_6COR_7$, $NR_6CO_2R_7$, $CR_6R_7OR_8$, $CONR_6R_7$, $CO_2R_6$, CN, $CF_3$, $NO_2$, $N_3$, C1-3 alkylthio, $R_9SO$, $R_9SO_2$, $CF_3S$, and $CF_3SO_2$;
$R_4$ is H or C1-10 alkyl;
$R_5$ is:

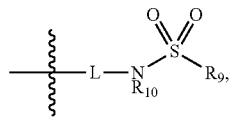

or an optionally substituted piperidine ring, connected through a carbon atom;
or $R_4$ and $R_5$ taken together form a piperidine ring with the nitrogen atom to which they are attached, wherein the piperidine ring is substituted with a substituent selected from the group consisting of $NR_6SO_2R_9$, $NR_6CONR_7R_{11}$, $NR_6COR_{15}$, and $NR_6CO_2R_7$ and is optionally further substituted with one or more substituents independently selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, and $CF_3SO_2$, $NR_6SO_2R_9$, $NR_6CONR_7R_{11}$, $NR_6CO_2R_7$, and $CONR_6R_7$;
or $R_4$ and $R_5$ taken together form an optionally substituted thiomorpholine 1,1-dioxide ring;
$R_6$, $R_7$, and $R_8$ are independently selected from H and optionally substituted C1-10 alkyl;
$R_9$ is H, optionally substituted C1-10 alkyl, $NR_6R_7$, or $NR_6COR_7$;
$R_{10}$ is H or optionally substituted C1-10 alkyl;
$R_{11}$ is selected from the group consisting of H, optionally substituted C1-10 alkyl, and $CR_6R_7CO_2R_8$;
$R_{15}$ is optionally substituted C1-12 alkyl, optionally substituted C1-12 heteroalkyl, optionally substituted C1-6alkyl(amino), or optionally substituted aryl;
L is a linker comprising an optionally substituted C1-15 alkyl or C1-15 heteroalkyl;
m and n are each independently integers from 0 to 5;
or a pharmaceutically acceptable ester, amide, salt, solvate, prodrug, or isomer thereof.

In one embodiment, L can comprise, for example, a cyclohexyl group. For example, L can be $CH_2$—$C_6H_{10}$—$CH_2$. In certain embodiments, $R_{10}$ is H. In certain embodiments, $R_9$ is selected from $CH_3$ and $NH_2$.

In some embodiments, $R_4$ is H. In certain embodiments, $R_4$ and $R_5$ taken together form a piperidine ring with the nitrogen atom to which they are attached. In certain embodiments, the piperidine ring is substituted at the 4 position with one or two substituents and may be optionally substituted at other positions on the piperidine ring. In certain embodiments, one piperidine substituent at the 4 position is a phenyl group and the other piperidine substituent at the 4 position is selected from the group consisting of $NR_6SO_2R_9$, $NR_6CONR_7R_8$, and $NR_6CO_2R_7$. In certain embodiments, one piperidine substituent (e.g., at the 4 position) is a sulfamide or sulfonamide, $NR_6SO_2R_9$ (e.g., $NHSO_2CH_3$). In certain embodiments, one piperidine substituent (e.g., at the 4 position) is a carbamate, $NR_6CO_2R_7$ (e.g., NHC(O)O-t-butyl). In certain embodiments, one piperidine substituent (e.g., at the 4 position) is a urea, $NR_6CONR_7R_8$. In some exemplary urea substituents, $R_6$ and $R_7$=H. In certain urea substituents, $R_{11}$ is an alkyl, selected from the group consisting of ethyl, propyl (n-propyl and isopropyl), butyl (n-butyl, sec-butyl, isobutyl, or t-butyl). In certain embodiments, the $R_{11}$ alkyl can comprise one or more cyclo alkyl groups.

In other embodiments, the invention provides a compound according to Formula II:

Formula II

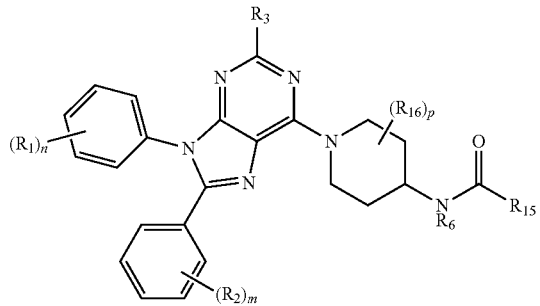

wherein $R_1$, $R_2$, $R_3$, and $R_6$ are as defined above with regard to Formula I;
$R_{15}$ is optionally substituted C1-12 alkyl, optionally substituted C1-12 heteroalkyl, optionally substituted C1-6alkyl (amino), or optionally substituted aryl;
$R_{16}$ is selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, and $CF_3SO_2$, $NR_6SO_2R_9$, $NR_6CONR_7R_{11}$, $NR_6CO_2R_7$, and $CONR_6R_7$; and
p is an integer from 0-9,
or a pharmaceutically acceptable ester, amide, salt, solvate, prodrug, or isomer thereof.

In certain embodiments of Formulas I and II, $R_{15}$ comprises one or more cyclic or heterocyclic rings (e.g., cyclohexyl, cyclopentyl, or piperidine). In somes specific embodiments, $R_{15}$ is selected from the group consisting of cyclohexyl, n-butyl, cyclohexylmethyl, isobutyl, cyclopentyl, 3-methylbutyl, cyclopentylmethyl, (piperidin-1-yl)ethyl, and $Me_2NCH_2$. In some embodiments of Formula II, p=0.

In certain embodiments of Formulas I and II, n is 1 and the $R_1$ substituent is at the para position and m is 1 and the $R_2$ substituent is at the ortho position. In some embodiments, $R_1$ and $R_2$ are both halo substituents (e.g., Cl). In certain embodiments, $R_3$ is H. $R_6$ in certain embodiments of Formulas I and II is H.

Certain compounds according to Formulas I and II are compounds with relatively high topological polar surface areas ("TPSA"s). TPSA has been shown to correlate to passive transport through membranes. In certain embodiments, it is desirable to provide compounds with minimal blood-brain barrier penetration. Such compounds may target peripheral receptors and thus reduce potential central nervous system-related side effects. Generally, higher TPSA values correspond to lower penetration into the CNS and may thus be desirable.

A TPSA can be calculated for any given compound to predict that compound's ability to penetrate the blood-brain barrier. Various methods can be used for such calculations and predictions, such as computational models. For example, methods for calculating molecular polar surface area as a sum of fragment based contributions are described in Ertl et al., *J. Med. Chem.* 43: 3714-3417 (2000), which is incorporated herein by reference. In certain embodiments, TPSA values for compounds are calculated using commercially available software from Advanced Chemistry Development (ACD 10, ACD/ChemSketch). In some preferred embodiments, compounds of Formulas I and/or II are provided, wherein the TPSAs of such compounds are greater than that of otenabant (i.e., greater than about 50). For example, in certain embodiments, the TPSAs of compounds according to the present invention are greater than about 55, greater than about 60, greater than about 65, greater than about 70, or greater than about 75. Certain compounds may exhibit TPSAs of greater than about 80, greater than about 90, or greater than about 100.

Accordingly, in certain embodiments of the present invention, compounds are provided which exhibit relatively low penetration through the blood-brain barrier. For example, compounds may preferably exhibit lower penetration through the blood-brain barrier than rimonabant. Penetration of compounds can be measured by any means, including, but not limited to: in vivo methods such as intravenous injection/brain sampling, brain uptake index, brain perfusion, quantitative autoradiography, external registration (MRI, SPECT, PET), microdialysis, or CSF sampling; and in vitro methods such as binding, uptake, and efflux measurements on fresh isolated brain microvessels and endothelial cell cultures. Reviews of various methods for prediction and measurement of blood-brain barrier penetration can be found in Bickel, *NeuroRx®* 2:15-26 (2005) and Liu, *Drug Metabolism and Disposition* 32(1): 132-139 (2004), which are both incorporated herein by reference.

In certain embodiments, pyrimidine-containing compounds of Formula IA, as well as pharmaceutically acceptable esters, amides, salts, solvates, prodrugs, and isomers thereof are provided, according to the following structure.

Formula IA

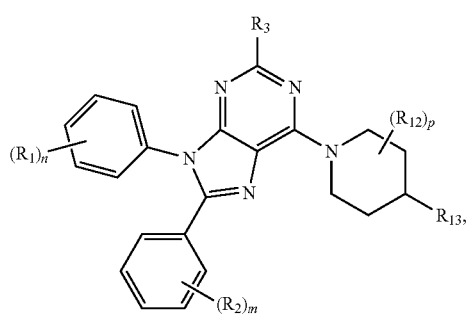

wherein $R_{12}$ is selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, and $CF_3SO_2$, $NR_6SO_2R_9$, $NR_6CONR_7R_{11}$, $NR_6CO_2R_7$, and $CONR_6R_7$;

$R_{13}$ is selected from the group consisting of $NR_6SO_2R_9$, $NR_6CONR_7R_{11}$, $NR_6COR_{15}$, and $NR_6CO_2R_7$;

and p is an integer from 0-9.

In compounds according to Formula IA, $R_{13}$ may be a sulfamide or sulfonamide, $NR_6SO_2R_9$ (e.g., $NHSO_2CH_3$), a carbamate, $NR_6CO_2R_7$ (e.g., NHC(O)O-t-butyl), or a urea, $NR_6CONR_7R_8$. In some exemplary urea substituents, $R_6$ and $R_7$=H. In certain urea substituents, $R_{11}$ is an alkyl, selected from the group consisting of ethyl, propyl (n-propyl and isopropyl), butyl (n-butyl, sec-butyl, isobutyl, or t-butyl). In certain embodiments, p=1 and the $R_{12}$ substituent is attached to the same carbon as $R_{13}$. In some embodiments, $R_{12}$ is aryl (e.g., phenyl) or optionally substituted aryl (e.g., optionally substituted phenyl).

In certain embodiments, sulfamide- or sulfonamide-containing compounds of Formula IA, as well as pharmaceutically acceptable esters, amides, salts, solvates, prodrugs, and isomers thereof are provided, according to the following structure, Formula IB.

Formula IB

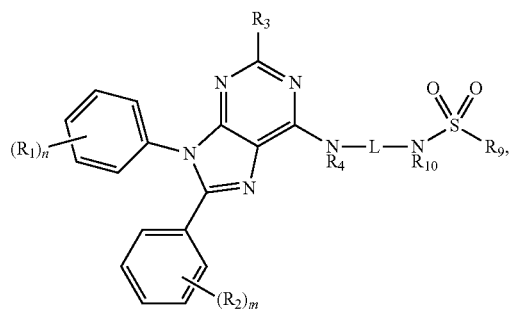

As noted above, the length and the chemical makeup of the linker group L between the purine fused ring system and the sulfamide or sulfonamide group can vary. In certain exemplary compounds, L comprises one or more linear and/or cycloalkyl groups. For example, Formula IB(1), below, is an exemplary subset of compounds of Formula IB, wherein L comprises a cyclohexyl subunit within a linear alkyl linker.

Formula IB(1)

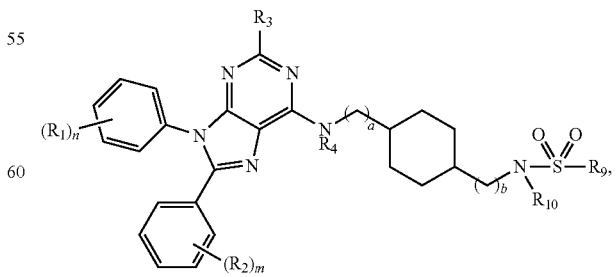

wherein a and b are integers independently selected from 0 to 9. In certain embodiments, both a and b are 1.

In some embodiments, thiomorpholine 1,1-dioxide-containing compounds of Formula IC, as well as pharmaceutically acceptable esters, amides, salts, solvates, prodrugs, and isomers thereof are provided according to the following structure:

Formula IC

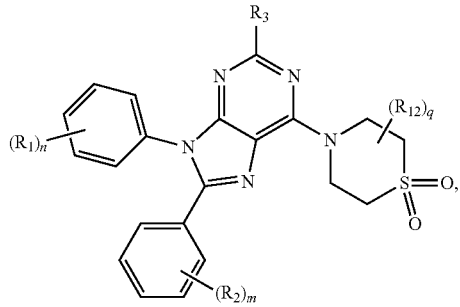

wherein $R_{12}$ is selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, $CF_3SO_2$, $NR_6SO_2R_9$, $NR_6CONR_7R_{11}$, $NR_6CO_2R_7$, and $CONR_6R_7$; and q is an integer from 0-9. In certain embodiments, q=0.

In certain embodiments, piperidine-containing compounds of Formula ID, as well as pharmaceutically acceptable esters, amides, salts, solvates, prodrugs, and isomers thereof are provided, according to the following structure.

Formula ID

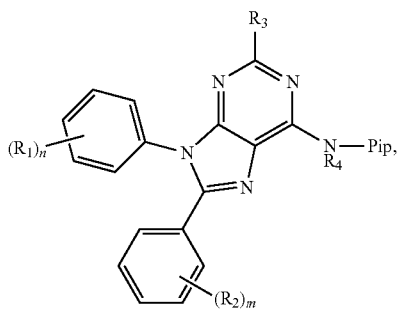

wherein Pip is an optionally substituted piperidine ring, connected through a carbon atom. In certain embodiments, the N of the piperidine ring is meta or para to the connection to the N adjacent to the purine moiety.

Certain exemplary configurations of the piperidine ring of Formula ID are illustrated below, in Figures ID(1) and ID(2):

Formula ID(1)

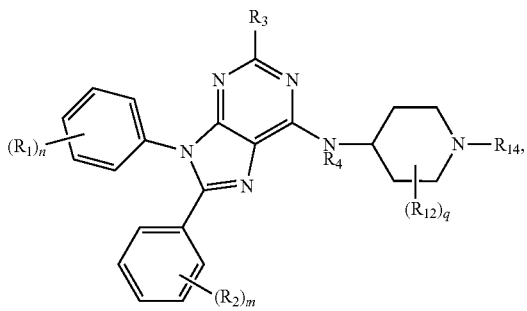

Formula ID(2)

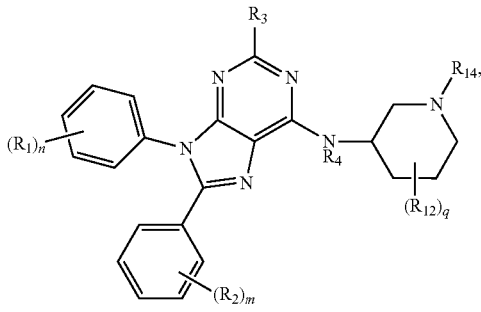

wherein $R_{12}$ is selected from the group consisting of halo, OH, optionally substituted C1-10 alkyl, optionally substituted C1-10 alkoxy, optionally substituted C2-4 alkenyl, optionally substituted C2-4 alkynyl, optionally substituted aryl (e.g., phenyl), optionally substituted aralkyl, optionally substituted alkaryl, $NR_6R_7$, $NR_6COR_7$, $CR_6R_7OR_8$, $CO_2R_6$, CN, $CF_3$, $NO_2$, $N_3$, C1-3 alkylthio, $R_9SO$, $R_9SO_2$, $CF_3S$, $CF_3SO_2$, $NR_6SO_2R_9$, $NR_6CONR_7R_{11}$, $NR_6CO_2R_7$, and $CONR_6R_7$;

$R_{14}$ is selected from the group consisting of H, optionally substituted C1-10 alkyl, $CR_6R_7OR_8$, $CONR_6R_7$, $C(O)OR_6$, $C(O)R_6$, $SOR_9$, and $SO_2R_9$; and q is an integer from 0-9. In certain embodiments, q=0.

The compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

In some embodiments, the compounds of Formula I are racemic. In some embodiments, compounds with one or more chiral centers are provided. While racemic mixtures of compounds of the invention can be active, selective, and bioavailable, isolated isomers may be of interest as well. The compounds of the present invention optionally may be provided in a composition that is enantiomerically enriched, such as a mixture of enantiomers in which one enantiomer is present in excess, in particular to the extent of 95% or more, or 98% or more, including 100%.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The terms (R) and (S) as used herein mean that the composition contains a greater proportion of the named isomer of the compound in relation to other isomers. In a preferred embodiment these terms indicate that the composition contains at least 90% by weight of the named isomer and 10% by weight or less of the one or more other isomers; or more preferably about 95% by weight of the named isomer and 5% or less of the one or more other isomers. These percentages are based on the total amount of the compound of the present invention present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the compounds of the present invention include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free moiety, e.g., amine and/or carboxylic acid moiety. Any of these can be used in combination with the disclosed active agents to achieve a desired effect.

Certain preferred compounds of the present invention include the following:

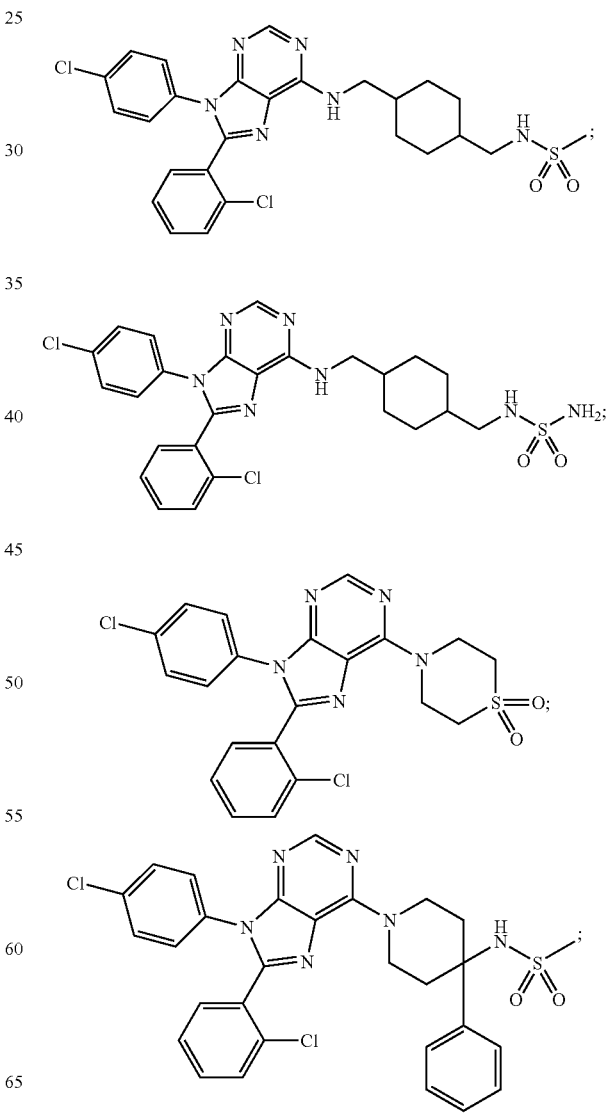

-continued
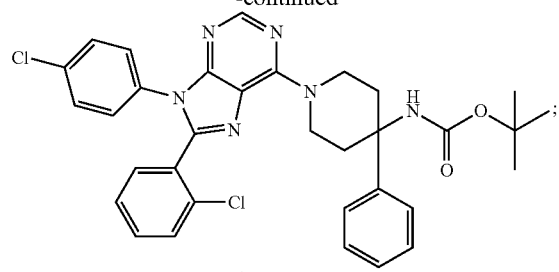
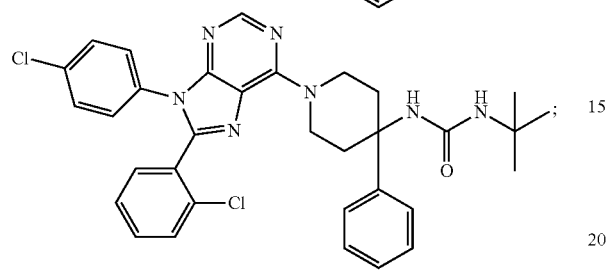
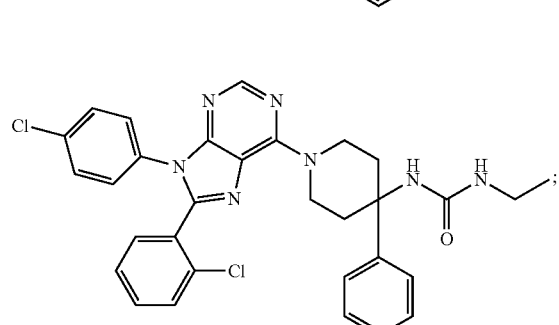
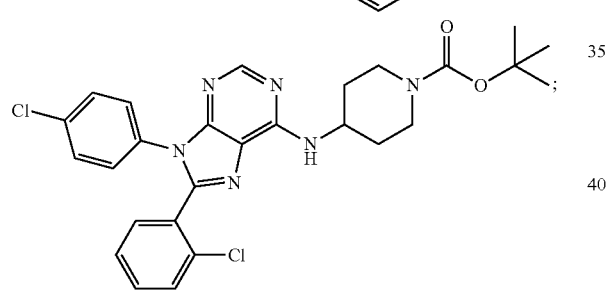
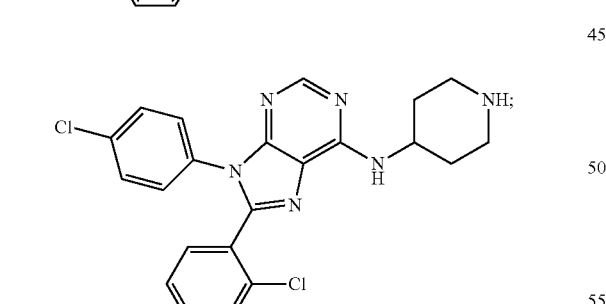
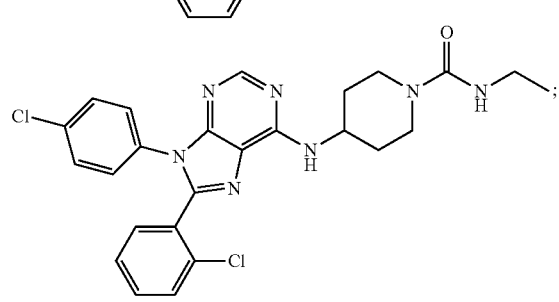
-continued
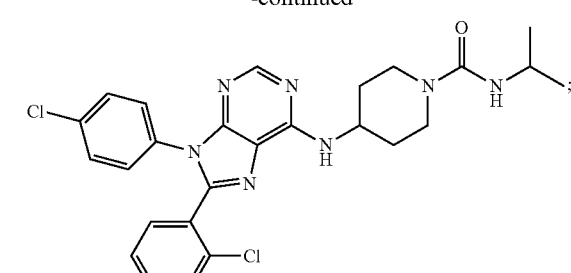
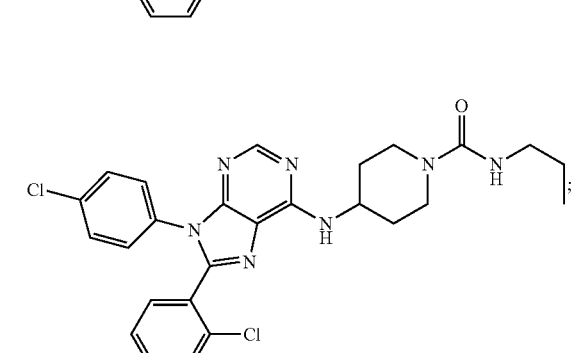
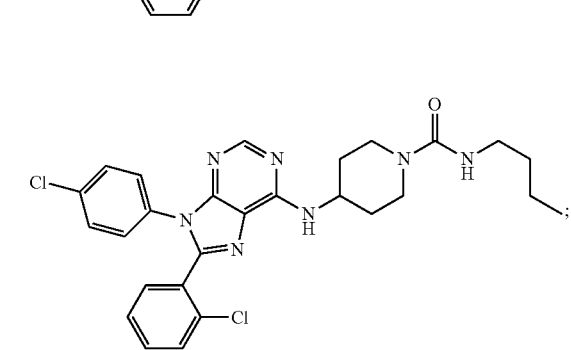
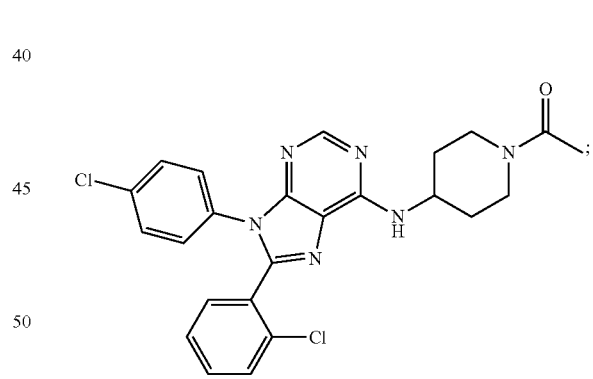
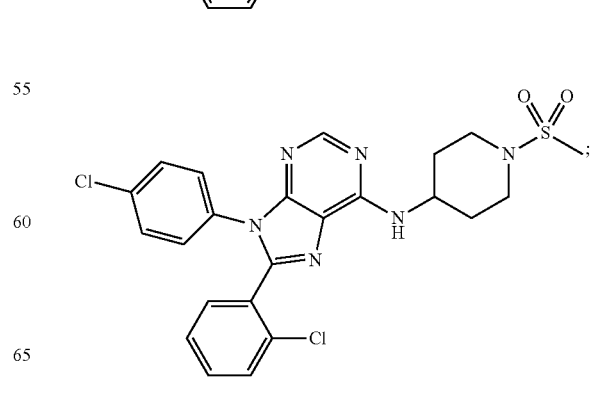

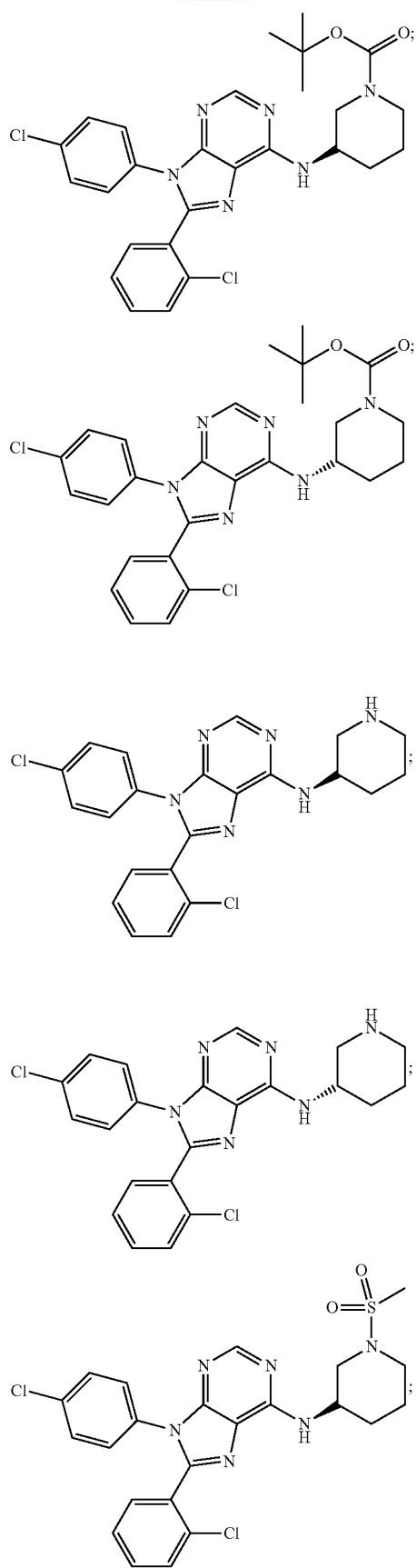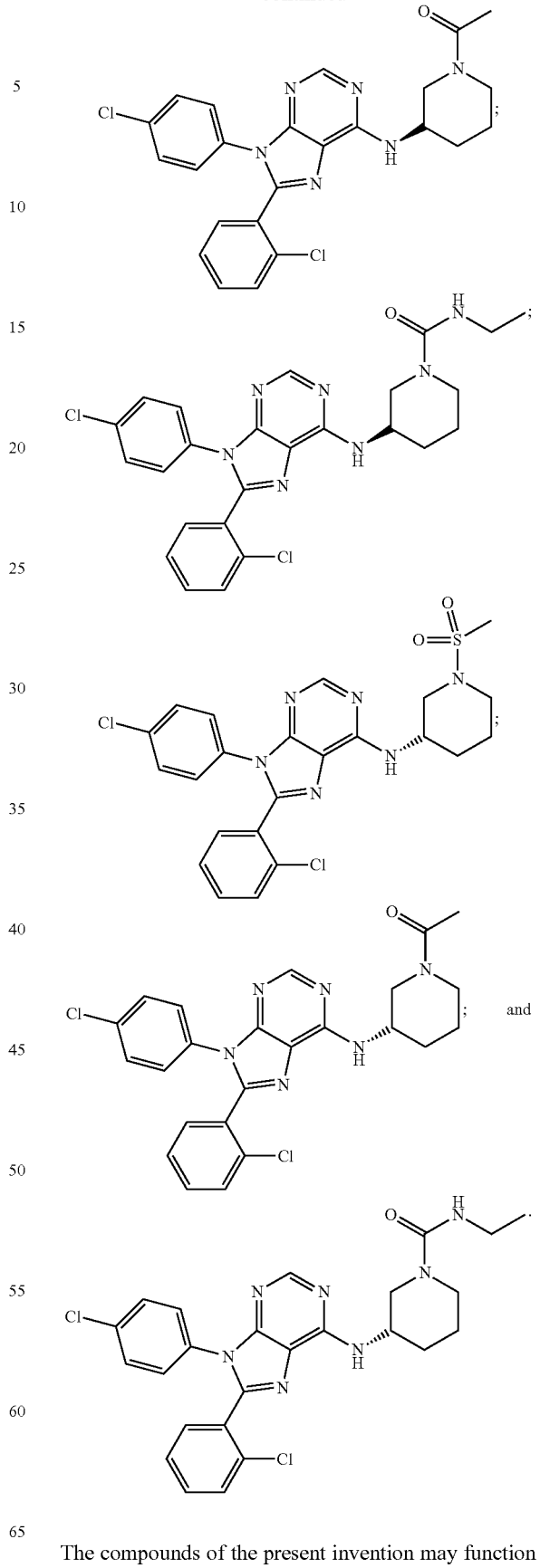
The compounds of the present invention may function as antagonists at the CB1 receptor, but preferably do not cross the blood-brain barrier. Thus, in certain embodiments, the compounds can be described as peripherally restricted CB1 antagonists. As noted, certain compounds of the present invention have high TPSA values. Compounds with high TPSA values typically exhibit lower penetration into the central nervous system (CNS), which may be beneficial according to the present invention. Certain compounds have hydrogens available for H bonding, providing the compounds with the ability to interact further with the receptor site, which may lead to improved potency of such compounds. In certain embodiments, the compounds are tailored so as to maximize the TPSA to preclude CNS permeability, but ensuring a reasonable level of oral bioavailability to allow for oral uptake. In preferred embodiments, the compounds of the present invention are selective for the CB1 receptor.

Methods of Preparation

The present invention also encompasses methods of preparing compounds with structures represented by Formulas I and II. One of skill in the art would be able to adapt these methods as required to accommodate various functional groups that may affect the chemistry of the synthesis.

In certain embodiments, compounds of the present invention can be prepared according to the following schemes. Scheme 1 illustrates possible synthetic methods for (a) the preparation of certain piperidine-containing analogues, (b) the preparation of N-alkyl intermediates by nucleophilic aromatic substitution, which can be converted to compounds of the present invention, for example, by (c) reaction with a sulfonyl chloride to give a sulfonamide or by (d) reaction with diamino sulfonic acid to give a sulfamide.

Scheme 1:
a)

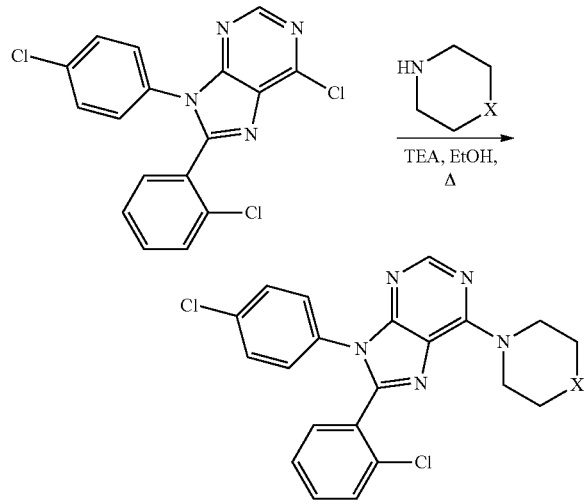

b)

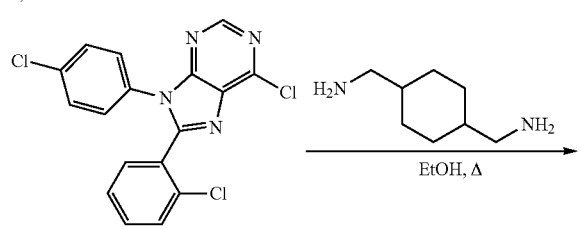

c)

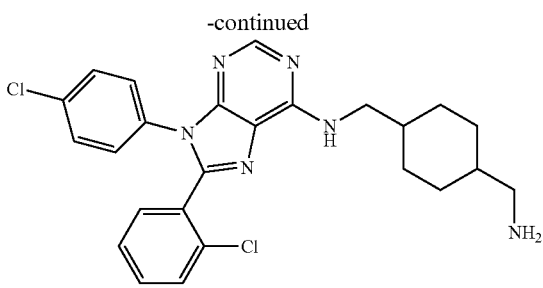

d)

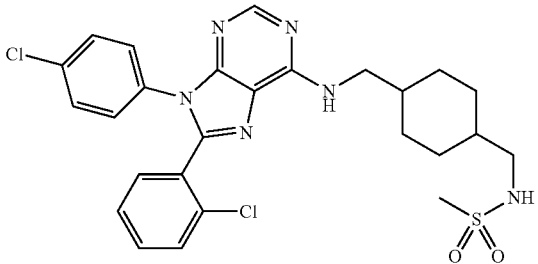

In certain embodiments, compounds of the invention can be prepared according to Scheme 2, which shows synthetic routes for the preparation of various piperidine-containing sulfonamides, carbamates, and ureas of the present invention.

Generally, in step a), a purine derivative is subjected to reaction with a functionalized piperidine to give a purine derivative with an amine functionalized piperidine attached thereto. The amine can be further functionalized, for example, as shown in step b) with a sulfonyl chloride to give a sulfonamide group, or in c) with an isocyanate to give a urea.

Scheme 2:

a)

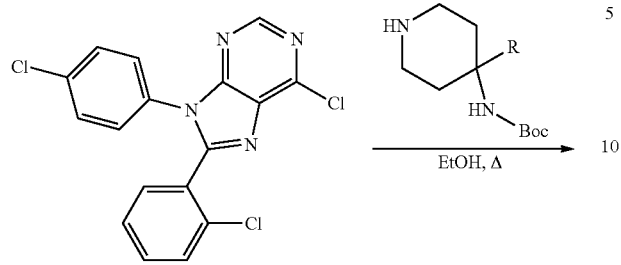

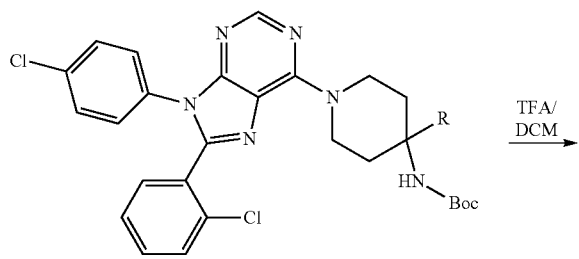

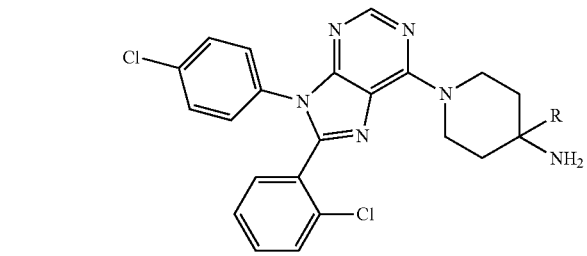

b)

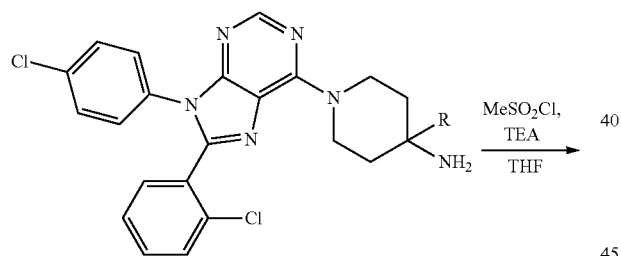

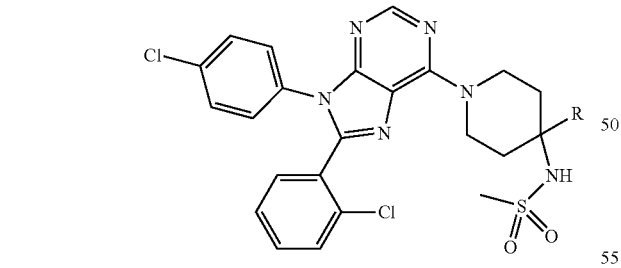

c)

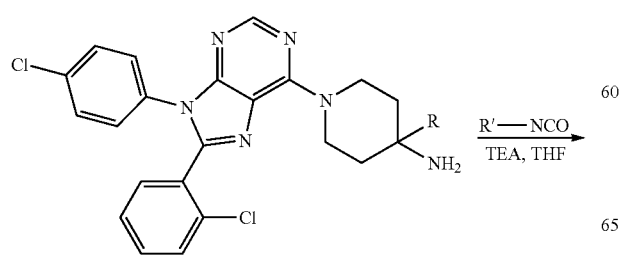

-continued

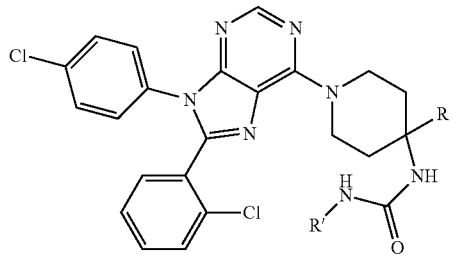

In certain embodiments, compounds of the invention can be prepared according to Scheme 3, which shows synthetic routes for the preparation of various piperidine-containing sulfonamides, carbamates, and ureas of the present invention.

Generally, in step a), a purine derivative is subjected to reaction with a functionalized piperidine to give a purine derivative with a piperidine functionalized amine attached thereto. The piperidine nitrogen can be further functionalized, for example, as shown in step b) with a sulfonyl chloride to give a sulfonamide group, or in c) with an isocyanate to give a urea.

Scheme 3:

a)

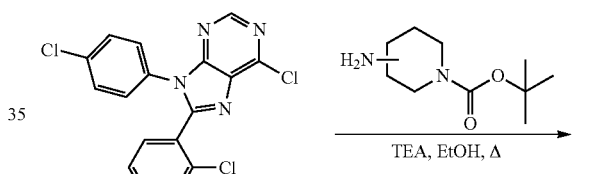

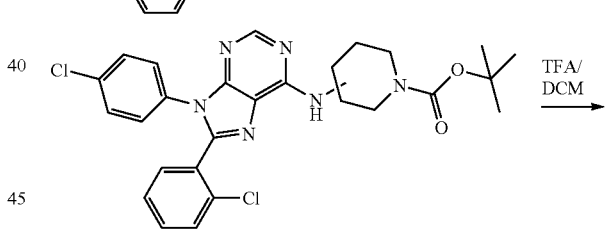

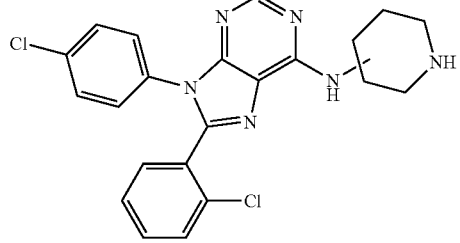

b)

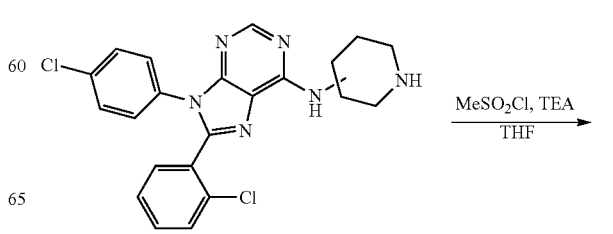

-continued

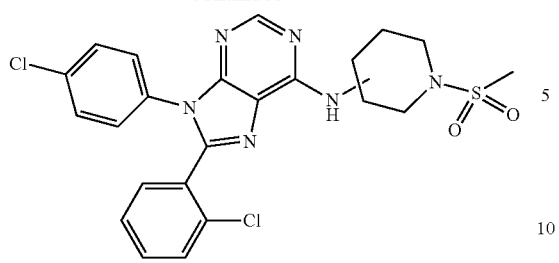

c)

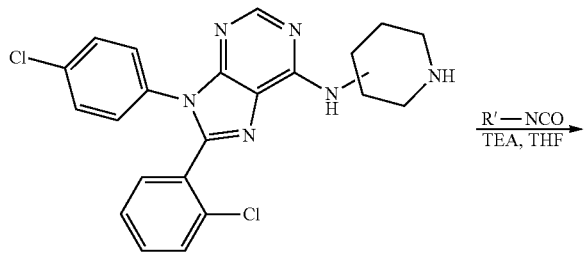

R'—NCO
TEA, THF

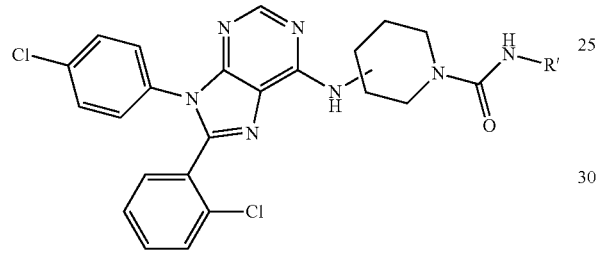

-continued

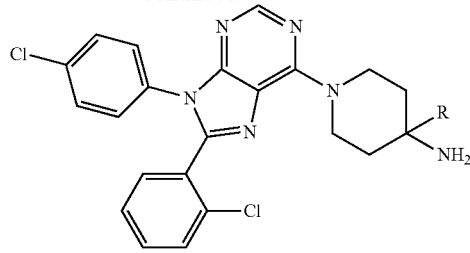

b)

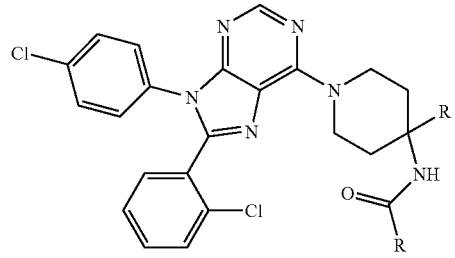

appropriate carboxylic acid or amino acid, benzotriazol-1-yloxy)tris (dimethylamino) phosphonium hexafluorophosphate (BOP), TEA, THF Compounds of Formula II can be prepared, for example, according to Scheme 4. Generally, in step a), a purine derivative is subjected to reaction with a functionalized piperidine to give a purine derivative with an amine functionalized piperidine attached thereto. The amine can be further functionalized, for example, as shown in step b) with a carboxylic acid or amino acid to give an amide group.

Scheme 4:
a)

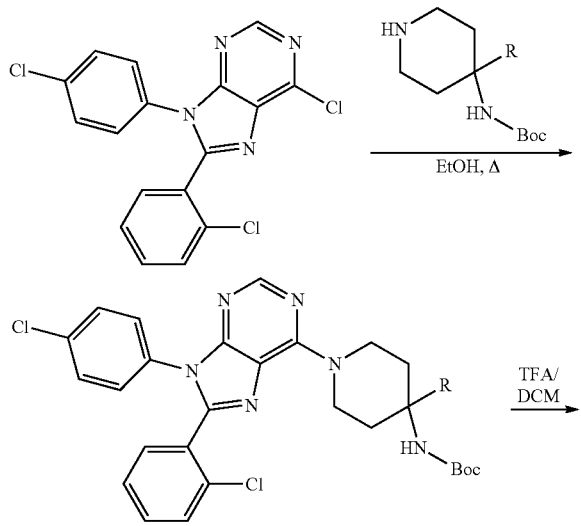

Compositions

While it is possible for the compounds (and/or pharmaceutically acceptable esters, amides, salts, solvates, prodrugs, and/or isomers thereof) of the present invention to be administered in the raw chemical form, it is preferred for the compounds to be delivered as a pharmaceutical formulation. Accordingly, there are provided by the present invention pharmaceutical compositions comprising at least one compound capable of functioning as an antagonist of the CB1 receptor. As such, the formulations of the present invention comprise a compound of Formula I or a compound of Formula II, as described above, or a pharmaceutically acceptable ester, amide, salt, solvate, prodrug, or isomer thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) J. Parent. Drug Assn. 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations).

Exemplary pharmaceutical excipients and/or additives suitable for use in the compositions according to the invention are listed in Remington: "The Science & Practice of Pharmacy," 21$^{st}$ ed. Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formulas I and II according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of Formula I and II above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of Formula I or II into association with a carrier that constitutes one or more accessory ingredients. In general, the compositions are prepared by bringing a compound of the invention into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula I or II in the formulation will vary depending the specific compound selected, dosage form, target patient population, and other considerations, and will be readily determined by one skilled in the art. The amount of the compound of Formula I or II in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds of the present invention comprise one or more compounds generally recognized as useful for treating the conditions discussed herein. In one embodiment, the use of two or more drugs, which may be of different therapeutic classes, may enhance efficacy and/or reduce adverse effects associated with one or more of the drugs.

For example, in certain embodiments, the present invention relates to the treatment of obesity. Accordingly, in one embodiment, a compound of Formula I or II is combined with one or more known antiobesity drugs for the treatment of obesity. Common therapeutic classes of obesity drugs include those that decrease food intake by either reducing appetite or increasing satiety, those that decrease nutrient absorption, and those that increase energy expenditure. Examples of known antiobesity drugs include: phentermine, which is an appetite suppressant; topiramate, which is an depressant/epilepsy drug that has been shown to interfere with binge eating and may result in decreased weight and decreased blood pressure; Orlistat (Xenical, Alli®), which reduces intestinal fat absorption by inhibiting pancreatic lipase; Sibutramine (Reductil or Meridia), which is an anorectic or appetite suppressant; diethylpropion (diethylcathinone/amfepramone, also sold as Anorex®, Tenuate®, and Tepanil®), which is a stimulant marketed as an appetite suppressant (which functions as a prodrug for ethcathinone); Mazindol (Mazanor, Sanorex), which is a tetracyclic stimulant drug used for short-term treatment of obesity; Rimonabant (Acomplia), which is a compound that is a cannabinoid (CB1) receptor antagonist that acts centrally on the brain to decrease appetite and may also increase energy expenditure; metformin (glucophage) in people with diabetes mellitus type 2; Exenatide (Byetta) and Pramlintide (Symlin), which both delay gastric emptying and promote a feeling of satiety. Other over-the-counter weight loss products including herbal remedies, laxatives, diet pills, diuretic drugs, and/or pyruvate may also be combined with the compounds disclosed herein. The compounds disclosed herein may also be used in combination with non drug-based therapy, including caloric restriction, exercise, and behavioral therapy.

Combinations of compounds of the present invention with other therapeutic agents are also included in the present invention, wherein the condition to be treated is any condition that may be responsive to the antagonism of the CB1 receptor.

For example, diabetes may be treated with compounds of the present invention, and thus, in one embodiment, a compound of Formula I or II is combined with one or more known drugs for the treatment of diabetes. In certain embodiments, diabetes is treated with compounds of the present invention in combination with insulin. Diabetes medications generally fall within six classes of drugs that work in different ways to lower blood glucose levels. Specifically, these medications include sulfonylureas, which stimulate the beta cells of the pancrease to release more insulin (e.g., chlorpropamide (Diabinese), glipizide (Glucotrol and Glucotrol XL), glyburide (Micronase, Glynase, and Diabeta, and glimepiride (Amaryl)); meglitinides, which stimulate the beta cells to release insulin (e.g., repaglinide (Prandin) and nateglinide (Starlix)); biguanides, which lower blood glucose levels primarily by reducing the glucose produced by the liver (e.g., metformin (Glucophage)); thiazolidinediones, which help insulin to work better in the muscle and fat, and also reduce glucose production in the liver (e.g., rosiglitazone (Avandia) and pioglitazone (ACTOS)); alpha-glucosidase inhibitors, which help lower blood glucose levels by blocking the breakdown of starches in the intestine and may slow the breakdown of some sugars (e.g., acarbose (Precose) and meglitol (Glyset)); and DPP-4 inhibitors, which prevent the breakdown of GLP-1, which is a naturally occurring compound in the body that reduces blood glucose levels (e.g., sitagliptin (Januvia) and saxagliptin (Onglyza).

Dyslipidemia may also be treated using compounds with the present invention. Thus, in one embodiment, a compound of Formula I or II is combined with one or more known drugs for the treatment of dyslipidemia. Medications for dyslipidemia typically fall into four classes of compounds capable of lowering lipid levels. These classes include statins, which are 3-hydroxy-3-methylglutaryl coenzyme A (HMG-CoA) reductase inhibitors (e.g.); fibrates, which reduce triglyceride and very low-density lipoprotein production in the liver (e.g., gemfibrozil, clofibrate, and fenofibrate); niacin (also known as nicotinic acid or Vitamin B3), which lowers total cholesterol and triglycerides and may also increase high-density lipoprotein cholesterol; and bile acid sequestering resins, which bind bile acids in the small intestine and prevent their return to the liver (e.g., cholestipol and cholestyramine).

Various liver diseases may be treated using compounds of the present invention. Accordingly, in one embodiment, a compound of Formula I or II is combined with one or more known drugs for the treatment of various types of liver disease. For example, exemplary medications used to treat fatty liver disease or nonalcoholic steatohepatitis include Actos, Avandia, Xenical, Actigall, Urso, Urso Forte, Orlostat, and Cystadane.

Further, in one embodiment, a compound of Formula I or II is combined with one or more known drugs for the treatment of pain and/or inflammation. Many such drugs are well known, and include, for example, acetaminophen (e.g., Tylenol and aspirin-free Excedrin); nonsteroidal anti-inflammatory drugs (NSAIDS, e.g., aspirin, Motrin, and Aleve); topical corticosteroids (e.g., Cortaid and Cortizone); corticosteroids (e.g., Deltasone, Hydeltrasol, and Solu-Medrol); opiods (e.g., morphine, fentanyl, oxycodone, and codeine); antidepressants (e.g., selective serotonin reuptake inhibitors (SSRIs) such as Celexa, Prozac, Paxil, and Zoloft; tricyclic antidepressants such as Elavil, Norpramin, Sinequan, Tofranil, and Pamelor; and selective serotonin and norepinephrine reuptake inhibitors (SSNRIs) such as Effexor and Cymbalta); and anticonvulsants (e.g., Tegretol, Neurontin, and Lyrica).

The compound of Formula I or II (and/or pharmaceutically acceptable ester, amide, salt, solvate, prodrug, and/or isomer thereof) and the one or more other therapeutic agents may be contained within a single composition or alternatively may be administered concurrently or sequentially (consecutively) in any order. For sequential administration, each of the compound of Formula I or II and the one or more other therapeutic agents can be formulated in its own pharmaceutical composition, each of which is to be administered sequentially, in any order. Alternatively, the compound of Formula I or II and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for treating or delaying the progression of disorders that are alleviated by antagonizing the CB1 receptors in a patient, the method comprising administering a therapeutically effective amount of at least one compound of Formula I or II to the patient.

In particular, the present invention relates to the field of treating obesity in animals, particularly humans and other mammals, and associated effects of these conditions. It also may relate to the treatment of other conditions that may benefit from the antagonism of CB1 receptors, such as liver diseases, dyslipidemia, pain/inflammation, and metabolic disorder. In some embodiments, the compounds show selectivity for CB1 over other cannabinoid receptors.

Obesity has its common meaning, e.g., the medical condition that exists when an individual has accumulated excess body fat, which may lead to a variety of related health problems, and which is characterized by a body mass index (BMI) of 30 kg/m$^2$ or more. Pre-obesity, also known as overweight, refers to the condition wherein an individual's BMI is between 25 kg/m$^2$ and 30 kg/m$^2$.

The method of treatment generally includes administering a therapeutically effective amount of a compound of Formula I or II, optionally in a pharmaceutical composition including one or more pharmaceutically acceptable carriers. The therapeutically effective amount is preferably sufficient to antagonize the CB1 receptor. The therapeutically effective amount is further preferably sufficient to cause some relief to the patient in the symptoms of the disorder for which the patient is being treated.

For example, in one embodiment, a method of treating obesity is provided. In such methods, a therapeutically effective amount of a compound of the present invention to treat a patient with pre-obesity or obesity may be that amount capable of antagonizing the CB1 receptor. Such compound may cause the patient to experience decreased appetite and/or may create a sensation of fullness. The method of treating obesity may be used to attain or maintain a patient's weight loss.

In another embodiment, a method of treating liver disease is provided. The liver disease may be, for example, fatty liver disease or nonalcoholic steatohepatitis (e.g., obesity-related steatosis). For example, compounds of the present invention can, in some embodiments, be used to slow the development of fatty liver (alcoholic or non-alcoholic fatty liver) and, in some cases, prevent the progression of fatty liver to more severe forms of liver disease. In some embodiments, compounds of the present invention may function to provide hepatoprotective activity. In some embodiments, the compounds may be capable of modulating lipid levels, reducing cholesterol, free fatty acids, and/or triglycerides.

In some embodiments, a method of treating diabetes is provided. Diabetes can be type 1, type 2, pre-diabetes, gestational diabetes, or latent autoimmune diabetes of adults (LADA). In some cases, the diabetes is associated with a disorder that has caused damage to the pancreas, such as cystic fibrosis, chronic pancreatitis, or haemochromatosis.

In some embodiments, a method of treating metabolic syndrome, a cluster of conditions such as high blood sugar and high triglycerides that can lead to cardiovascular disease, is provided. In certain other embodiments, a method of smoking cessation and/or a method for preventing weight gain in former smokers is provided.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compounds of the invention may be therapeutically effective. Furthermore, the therapeutically effective amount may vary depending on the specific condition to be treated.

The compounds of the invention can be administered once or several times a day. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

The compounds of the invention may be used with other types of therapy, including those which are non-drug based. Thus, in some embodiments, the methods of the present invention comprise administering to a subject a compound that that is capable of functioning as an antagonist of CB1 receptors in conjunction with one or more other types of non-drug-based therapy.

EXPERIMENTAL SECTION

Synthetic and characterization data is provided below for various compounds intended to be encompassed within various embodiments of the invention. It is noted that not all of the compounds described within the Experimental Section are included within the general genus structure of Formula I or II as provided above. However, such compounds are intended to be included as further alternative embodiments of the invention and the application should be read as such. Thus, the application should be construed as directed not only to compounds that fall within Formula I or II, but also to compounds that are specifically referenced within the Experimental section.

For example, in Table 1, a structure is provided, where "X" is a substituent that is varied to obtain different compounds. Compounds according to Formula I having each of the X substitutents recited in this table are also intended to be encompassed herein. Thus, these X groups can be considered to be, in certain embodiments, components of not only the specific structure provided in Table 1, but also components of the broader genus set forth in Formulas I and II (i.e., compounds provided in Table 1 are included within the present invention as well as analogues thereof, comprising other substituents at various locations within the molecule, as provided for within Formulas I and II).

Example 1

Synthesis

Purity and characterization of compounds were established by a combination of HPLC, TLC, and NMR analytical techniques described below. $^1$H spectra were recorded on a Bruker Avance DPX-300 (300 MHz) spectrometer and were determined in CHCl$_3$-d or MeOH-d4 with tetramethylsilane (TMS) (0.00 ppm) or solvent peaks as the internal reference unless otherwise noted. Chemical shifts are reported in ppm relative to the solvent signal, and coupling constant (J) values are reported in hertz (Hz). Thin-layer chromatography (TLC) was performed on EMD precoated silica gel 60 F254 plates, and spots were visualized with UV light or I$_2$ detection. Low-resolution mass spectra were obtained using a Waters Alliance HT/Micromass ZQ system (ESI). All test compounds were greater than 95% pure as determined by HPLC on an Agilent 1100 system using an Agilent Zorbax SB-Phenyl, 2.1×150 mm, 5 μm column with gradient elution using the mobile phases (A) H$_2$O containing 0.05% CF$_3$COOH and (B) Methanol. A flow rate of 1.0 mL/min was used.

1-[8-(2-Chlorophenyl)-9-(4-chlorophenyl)-9H-purin-6-yl]-4-phenylpiperidine-4-carboxamide. To a solution of 6-chloro-8-(2-chlorophenyl)-9-(4-chlorophenyl)-9H-purine (23.1 mg, 0.062 mmol, 1 eq.) in 2 mL of ethanol was added 4-carbamoyl-4-phenylpiperidin-1-ium trifluoroacetate (25 mg, 0.123 mmol, 2 eq.) and triethylamine (0.03 mL, 0.19 mmol, 3 eq.). The reaction was heated to 55° C. for 3 d. The reaction was concentrated in vacuo. The crude material was purified by silica gel column chromatography using 0-100% ethyl acetate/hexanes to yield 21 mg (63%) of 1-[8-(2-chlorophenyl)-9-(4-chlorophenyl)-9H-purin-6-yl]-4-phenylpiperidine-4-carboxamide. $^1$H NMR (300 MHz, METHANOL-d$_4$) δ ppm 2.02-2.21 (m, 2H) 2.62 (d, J=13.37 Hz, 2H) 3.82 (br. s., 2H) 4.98 (d, J=15.54 Hz, 2H) 7.07-7.67 (m, 13H) 8.02-8.29 (m, 1H), [M+H]$^+$ 543.6.

N-{[4-({[8-(2-Chlorophenyl)-9-(4-chlorophenyl)-9H-purin-6-yl]amino}methyl)cyclohexyl]methyl}methanesulfonamide. To a solution of 6-chloro-8-(2-chlorophenyl)-9-(4-chlorophenyl)-9H-purine (78 mg, 0.21 mmol, 1 eq.) in 2 mL of dioxane was added [4-(aminomethyl)cyclohexyl]methanamine (89 mg, 0.62 mmol, 2 eq.). The reaction was heated to 80° C. for 16 h. The reaction was concentrated in vacuo. The crude material was purified by silica gel column chromatography using 0-100% CMA 80/ethyl acetate to yield 76 mg (76%) of N-{[4-(aminomethyl)cyclohexyl]methyl}-8-(2-chlorophenyl)-9-(4-chlorophenyl)-9H-purin-6-amine which was carried forward. $^1$H NMR (300 MHz, CHLOROFORM-d) δ ppm 0.85-1.13 (m, 2 H) 1.40-1.72 (m, 8 H) 1.74-2.01 (m, 2 H) 2.85-3.15 (m, 2 H) 3.48-3.75 (m, 2 H) 4.25-4.74 (m, 2 H) 5.98 (br. s., 1 H) 7.05-7.59 (m, 8 H) 8.44 (s, 1 H).

To a solution of N-{[4-(aminomethyl)cyclohexyl]methyl}-8-(2-chlorophenyl)-9-(4-chlorophenyl)-9H-purin-6-amine (6 mg, 0.013 mmol, 1 eq.) in 5 mL of THF was added methanesulfonyl chloride (0.02 mL) and triethylamine (0.05 mL). The reaction was stirred at room temperature 16 h. The reaction was concentrated in vacuo. The crude material was purified by silica gel column chromatography using 0-100% ethyl acetate/hexanes to yield 5 mg (71%) of N-{[4-({[8-(2-chlorophenyl)-9-(4-chlorophenyl)-9H-purin-6-yl]amino}methyl)cyclohexyl]methyl}methanesulfonamide. $^1$H NMR (300 MHz, CHLOROFORM-d) δ ppm 0.82-1.16 (m, 2 H) 1.33-1.75 (m, 6 H) 1.77-2.02 (m, 2 H) 2.84-3.00 (m, 4 H) 3.00-3.16 (m, 1 H) 3.43-3.80 (m, 2 H) 4.40-4.63 (m, 1 H) 5.89-6.18 (m, 1 H) 7.08-7.60 (m, 8 H) 8.44 (s, 1 H), [M+H]$^+$ 559.6.

N-{[4-({[8-(2-Chlorophenyl)-9-(4-chlorophenyl)-9H-purin-6-yl]amino}methyl)cyclohexyl]methyl}aminosulfonamide. To a solution of N-{[4-(aminomethyl)cyclohexyl]methyl}-8-(2-chlorophenyl)-9-(4-chlorophenyl)-9H-purin-6-amine (6.6 mg, 0.014 mmol, 1 eq.) in 5 mL of dioxane was added 10 mg of sulfamide. The reaction was heated to 80° C. and stirred 16 h. The reaction was concentrated in vacuo. The crude material was purified by silica gel column chromatography using 0-100% ethyl acetate/hexanes to yield 1.9 mg (25%) of N-{[4-({[8-(2-chlorophenyl)-9-(4-chlorophenyl)-9H-purin-6-yl]amino}methyl)cyclohexyl]methyl}aminosulfonamide. $^1$H NMR (300 MHz, METHANOL-d$_4$) δ ppm 0.80-1.17 (m, 2 H) 1.21-1.79 (m, 6 H) 1.93 (br. s., 2 H) 3.00 (d, J=7.16 Hz, 2 H) 3.59 (br. s., 2 H) 7.19-7.69 (m, 8 H) 8.13-8.35 (m, 1 H), [M+H]$^+$ 562.2.

4-[8-(2-Chlorophenyl)-9-(4-chlorophenyl)-9H-purin-6-yl]-1λ$^6$,4-thiomorpholine-1,1-dione. To a solution of 6-chloro-8-(2-chlorophenyl)-9-(4-chlorophenyl)-9H-purine (19 mg, 0.051 mmol, 1 eq.) in 2 mL of ethanol was added 1λ$^6$,4-thiomorpholine-1,1-dione (14 mg, 0.10 mmol, 2 eq.).

The reaction was heated to 80° C. for 16 h. The reaction was concentrated in vacuo. The crude material was purified by silica gel column chromatography using 0-100% ethyl acetate/hexanes to yield 21 mg (88%) of 4-[8-(2-chlorophenyl)-9-(4-chlorophenyl)-9H-purin-6-yl]-1λ⁶,4-thiomorpholine-1,1-dione. ¹H NMR (300 MHz, CHLOROFORM-d) δ ppm 3.20 (br. s., 4 H) 4.87 (br. s., 4 H) 6.95-7.58 (m, 8 H) 8.45 (s, 1 H), [M+H]⁺ 474.8.

tert-Butyl N-{1-[8-(2-chlorophenyl)-9-(4-chlorophenyl)-9H-purin-6-yl]-4-phenylpiperidin-4-yl}carbamate. To a solution of 6-chloro-8-(2-chlorophenyl)-9-(4-chlorophenyl)-9H-purine (50 mg, 0.133 mmol, 1 eq.) in 2 mL of ethanol was added tert-butyl N-(4-phenylpiperidin-4-yl)carbamate (44 mg, 0.16 mmol, 1.2 eq) and triethylamine (0.03 mL, 0.20 mmol, 1.5 eq.). The reaction was heated to 80° C. for 16 h. The reaction was concentrated in vacuo. The crude material was purified by silica gel column chromatography using 0-100% ethyl acetate/hexanes to yield 69 mg (84%) of tert-butyl N-{1-[8-(2-chlorophenyl)-9-(4-chlorophenyl)-9H-purin-6-yl]-4-phenylpiperidin-4-yl}carbamate. ¹H NMR (300 MHz, CHLOROFORM-d) δ ppm 1.31-1.49 (m, 9 H) 2.09-2.28 (m, 2 H) 2.43 (br. s., 2 H) 3.62 (br. s., 2 H) 4.96 (s, 1 H) 5.30 (br. s., 2 H) 7.03-7.61 (m, 13 H) 8.40 (s, 1 H), [M+H]⁺ 615.4.

1-[8-(2-Chlorophenyl)-9-(4-chlorophenyl)-9H-purin-6-yl]-4-phenylpiperidin-4-amine A solution of tert-butyl N-{1-[8-(2-chlorophenyl)-9-(4-chlorophenyl)-9H-purin-6-yl]-4-phenylpiperidin-4-yl}carbamate (2.65 g, 4.3 mmol) was stirred in dichloromethane (32 mL) and trifluoroacetic acid (8 mL) for 1.5 h. The reaction was concentrated in vacuo. The crude product was dissolved in ethyl acetate and washed with 3.8 M NaOH. The aqueous layer was extracted twice with ethyl acetate. The combined organic layer was washed with brine and dried with MgSO₄ to yield 2.21 g (99%) of pure 1-[8-(2-chlorophenyl)-9-(4-chlorophenyl)-9H-purin-6-yl]-4-phenylpiperidin-4-amine. 1H NMR (300 MHz, CHLOROFORM-d) δ ppm 1.87 (d, J=13.56 Hz, 2 H) 2.15-2.39 (m, 2 H) 3.82-4.11 (m, 2 H) 5.10 (br. s., 2 H) 7.11-7.62 (m, 13 H) 8.40 (s, 1 H), [M+H]⁺ 515.8.

N-{1-[8-(2-Chlorophenyl)-9-(4-chlorophenyl)-9H-purin-6-yl]-4-phenylpiperidin-4-yl}methanesulfonamide. To a solution of 1-[8-(2-chlorophenyl)-9-(4-chlorophenyl)-9H-purin-6-yl]-4-phenylpiperidin-4-amine (8.4 mg, 0.016 mmol, 1 eq.) in 2 mL of THF was added methane sulfonyl chloride (0.01 mL) and triethylamine (0.02 mL). The mixture was stirred for 16 h. The reaction was concentrated in vacuo. The crude material was purified by silica gel column chromatography using 0-100% ethyl acetate/hexanes to yield 8 mg (82%) of N-{1-[8-(2-chlorophenyl)-9-(4-chlorophenyl)-9H-purin-6-yl]-4-phenylpiperidin-4-yl}methanesulfonamide. ¹H NMR (300 MHz, CHLOROFORM-d) δ ppm 2.22 (s, 3 H) 2.30-2.44 (m, 2 H) 2.47-2.66 (m, 2 H) 4.20 (br. s., 2 H) 4.75 (s, 2 H) 7.08-7.64 (m, 13 H) 8.38 (s, 1 H), [M+H]⁺ 593.3.

General Procedure for Making Ureas from 1-[8-(2-chlorophenyl)-9-(4-chlorophenyl)-9H-purin-6-yl]-4-phenylpiperidin-4-amine To a solution of 1-[8-(2-chlorophenyl)-9-(4-chlorophenyl)-9H-purin-6-yl]-4-phenylpiperidin-4-amine (19 mg, 0.036 mmol, 1 eq.) in 2 mL of THF was added triethylamine (0.015 mL, 0.108 mmol, 3 eq.) and the appropriate isocyanate (1.5 eq). The reaction is stirred for 16 h. The reaction was concentrated in vacuo. The crude material was purified by silica gel column chromatography using 0-100% ethyl acetate/hexanes to yield pure compound.

3-tert-Butyl-1-{1-[8-(2-chlorophenyl)-9-(4-chlorophenyl)-9H-purin-6-yl]-4-phenylpiperidin-4-yl}urea. Reaction proceeded in 81% yield. ¹H NMR (300 MHz, CHLOROFORM-d) δ ppm 1.12 (s, 9 H) 2.13-2.27 (m, 2 H) 2.27-2.43 (m, 2 H) 3.67 (br. s., 2 H) 3.96 (br. s., 1 H) 4.78 (br. s., 1 H) 5.10-5.68 (m, 2 H) 7.07-7.63 (m, 13 H) 8.40 (s, 1 H), [M+H]⁺ 614.7.

1-{1-[8-(2-Chlorophenyl)-9-(4-chlorophenyl)-9H-purin-6-yl]-4-phenylpiperidin-4-yl}-3-ethylurea. Reaction proceeded in 81% yield. ¹H NMR (300 MHz, CHLOROFORM-d) δ ppm 0.85-1.01 (m, 3 H) 2.11-2.29 (m, 2 H) 2.30-2.47 (m, 2 H) 2.96-3.20 (m, 2 H) 3.64 (br. s., 2 H) 4.10-4.24 (m, 1 H) 5.00 (s, 1 H) 5.32 (d, J=14.41 Hz, 2 H) 7.10-7.60 (m, 13 H) 8.40 (s, 1 H), [M+H]⁺ 586.8.

1-{1-[8-(2-Chlorophenyl)-9-(4-chlorophenyl)-9H-purin-6-yl]-4-phenylpiperidin-4-yl}-3-(propan-2-yl)urea. Reaction proceeded in 79% yield. ¹H NMR (300 MHz, CHLOROFORM-d) δ ppm 0.94 (d, J=6.50 Hz, 6 H) 2.13-2.29 (m, 2 H) 2.29-2.42 (m, 2 H) 3.51-3.76 (m, 2 H) 3.95 (d, J=7.82 Hz, 1 H) 4.93 (s, 1 H) 5.32 (d, J=13.56 Hz, 2 H) 7.07-7.63 (m, 13 H) 8.40 (s, 1 H), [M+H]⁺ 600.7.

1-{1-[8-(2-Chlorophenyl)-9-(4-chlorophenyl)-9H-purin-6-yl]-4-phenylpiperidin-4-yl}-3-propylurea. Reaction proceeded in 88% yield. ¹H NMR (300 MHz, CHLOROFORM-d) δ ppm 0.64-0.77 (m, 3 H) 1.19-1.37 (m, 2 H) 2.10-2.27 (m, 2 H) 2.29-2.45 (m, 2 H) 2.87-3.08 (m, 2 H) 3.63 (br. s., 2 H) 4.28 (br. s., 1 H) 5.11 (s, 1 H) 5.36 (br. s., 2 H) 7.10-7.60 (m, 13 H) 8.40 (s, 1 H), [M+H]⁺ 600.5.

3-Butyl-1-{1-[8-(2-chlorophenyl)-9-(4-chlorophenyl)-9H-purin-6-yl]-4-phenylpiperidin-4-yl}urea. Reaction proceeded in 82% yield. ¹H NMR (300 MHz, CHLOROFORM-d) δ ppm 0.74-0.86 (m, 3 H) 1.11 (dq, J=14.79, 7.22 Hz, 2 H) 1.20-1.31 (m, 2 H) 2.11-2.27 (m, 2 H) 2.29-2.41 (m, 2 H) 3.05 (q, J=6.59 Hz, 2 H) 3.63 (br. s., 2 H) 4.22 (t, J=5.13 Hz, 1 H) 5.07 (s, 1 H) 5.34 (br. s., 2 H) 7.12-7.56 (m, 13 H) 8.40 (s, 1 H), [M+H]⁺ 614.7.

Ethyl 2-[({1-[8-(2-chlorophenyl)-9-(4-chlorophenyl)-9H-purin-6-yl]-4-phenylpiperidin-4-yl}-carbamoyl)amino]acetate. Reaction proceeded in 92% yield. ¹H NMR (300 MHz, CHLOROFORM-d) δ ppm 1.18-1.28 (m, 3 H) 2.11-2.29 (m, 2 H) 2.33-2.52 (m, 2 H) 3.64 (br. s., 2 H) 3.82-3.92 (m, 2 H) 4.09-4.24 (m, 2 H) 5.13 (br. s., 1 H) 5.23-5.52 (m, 2 H) 5.60 (s, 1 H) 7.05-7.59 (m, 13 H) 8.39 (s, 1 H), [M+H]⁺ 644.4.

3-{1-[8-(2-Chlorophenyl)-9-(4-chlorophenyl)-9H-purin-6-yl]-4-phenylpiperidin-4-yl}-1-cyclohexylurea. Reaction proceeded in 69% yield. ¹H NMR (300 MHz, CHLOROFORM-d) δ ppm 0.77-1.13 (m, 3 H) 1.15-1.36 (m, 3 H) 1.36-1.54 (m, 3 H) 1.56-1.76 (m, 1 H) 2.12-2.28 (m, 2 H) 2.29-2.42 (m, 2 H) 3.34-3.55 (m, 1 H) 3.65 (br. s., 2 H) 3.96-4.20 (m, 1 H) 4.96 (s, 1 H) 5.34 (br. s., 2 H) 7.06-7.61 (m, 13 H) 8.40 (s, 1 H), [M+H]⁺ 640.5.

N-{1-[8-(2-chlorophenyl)-9-(4-chlorophenyl)-9H-purin-6-yl]-4-phenylpiperidin-4-yl}acetamide. A solution of 1-[8-(2-chlorophenyl)-9-(4-chlorophenyl)-9H-purin-6-yl]-4-phenylpiperidin-4-amine (6 mg, 0.011 mmol, 1 eq.) in 1 mL of acetic anhydride and 1 mL of pyridine was stirred for 16 h. The reaction was concentrated in vacuo. The crude material was purified by silica gel column chromatography using 0-100% ethyl acetate/hexanes to yield 6 mg (95%) of desired N-{1-[8-(2-chlorophenyl)-9-(4-chlorophenyl)-9H-purin-6-yl]-4-phenylpiperidin-4-yl}acetamide. Compound was determined to be 95% pure by ¹H NMR. ¹H NMR (300 MHz, CHLOROFORM-d) δ ppm 1.95-2.11 (m, 3 H) 2.15-

2.39 (m, 2 H) 2.60 (d, J=13.56 Hz, 2 H) 3.69 (br. s., 2 H) 5.23 (br. s., 2 H) 5.71 (br. s., 1 H) 7.10-7.60 (m, 13 H) 8.31-8.48 (m, 1 H), [M−H]⁻ 554.5.

N-tert-Butyl-1-[8-(2-chlorophenyl)-9-(4-chlorophenyl)-9H-purin-6-yl]-4-phenylpiperidine-4-carboxamide. To a solution of 6-chloro-8-(2-chlorophenyl)-9-(4-chlorophenyl)-9H-purine (19 mg, 0.051 mmol, 1 eq.) in 2 mL of ethanol was added N-tert-butyl-4-phenylpiperidine-4-carboxamide (13.2 mg, 0.051 mmol, 1 eq.) and triethylamine (0.02 mL, 0.15 mmol, 3 eq.). The reaction was heated to 80° C. for 16 h. The reaction was concentrated in vacuo. The crude material was purified by silica gel column chromatography using 0-100% ethyl acetate/hexanes to yield 22 mg (72%) of N-tert-butyl-1-[8-(2-chlorophenyl)-9-(4-chlorophenyl)-9H-purin-6-yl]-4-phenylpiperidine-4-carboxamide. ¹H NMR (300 MHz, CHLOROFORM-d) δ ppm 1.14-1.32 (m, 9 H) 2.17 (s, 2 H) 2.39-2.58 (m, 2 H) 4.07 (s, 2 H) 5.01 (s, 2 H) 7.10-7.44 (m, 12 H) 7.51 (d, J=6.59 Hz, 1 H) 8.37 (s, 1 H), [M+H]⁺ 599.7.

tert-Butyl 4-{[8-(2-chlorophenyl)-9-(4-chlorophenyl)-9H-purin-6-yl]amino}piperidine-1-carboxylate. To a solution of 6-chloro-8-(2-chlorophenyl)-9-(4-chlorophenyl)-9H-purine (151 mg, 0.403 mmol, 1 eq.) in 4 mL of ethanol was added tert-butyl 4-aminopiperidine-1-carboxylate (96 mg, 0.483 mmol, 1.2 eq.) and triethylamine (0.08 mL, 0.6 mmol, 1.5 eq.). The reaction was heated to 80° C. for 16 h. The reaction was concentrated in vacuo. The crude material was purified by silica gel column chromatography using 0-100% ethyl acetate/hexanes to yield 203 mg (94%) of tert-butyl 4-{[8-(2-chlorophenyl)-9-(4-chlorophenyl)-9H-purin-6-yl]amino}piperidine-1-carboxylate. ¹H NMR (300 MHz, CHLOROFORM-d) δ ppm 1.38-1.55 (m, 11 H) 2.14 (d, J=12.34 Hz, 2 H) 2.98 (t, J=12.10 Hz, 2 H) 4.00-4.21 (m, 2 H) 4.28-4.52 (m, 1 H) 5.83 (d, J=7.63 Hz, 1 H) 7.17-7.27 (m, 2 H) 7.31-7.44 (m, 5 H) 7.50 (d, J=6.88 Hz, 1 H) 8.44 (s, 1 H), [M+H]⁺ 539.4.

8-(2-Chlorophenyl)-9-(4-chlorophenyl)-N-(piperidin-4-yl)-9H-purin-6-amine. A solution of tert-butyl 4-{[8-(2-chlorophenyl)-9-(4-chlorophenyl)-9H-purin-6-yl]amino}piperidine-1-carboxylate (180 mg, 0.33 mmol) was stirred in dichloromethane (9 mL) and trifluoroacetic acid (4 mL) for 16 h. The reaction was concentrated in vacuo. The crude product was dissolved in ethyl acetate and washed with saturated NaHCO₃. The aqueous layer was extracted twice with ethyl acetate. The combined organic layer was washed with brine and dried with MgSO₄. The crude material was purified by silica gel column chromatography using 0-100% CMA 80/ethyl acetate to yield 129 mg (88%) of 8-(2-chlorophenyl)-9-(4-chlorophenyl)-N-(piperidin-4-yl)-9H-purin-6-amine. ¹H NMR (300 MHz, CHLOROFORM-d) δ ppm 1.45 (qd, J=11.66, 3.81 Hz, 2 H) 2.10 (d, J=11.87 Hz, 2 H) 2.64-2.88 (m, 2 H) 3.10 (d, J=12.62 Hz, 2 H) 4.27 (br. s., 1 H) 5.80 (d, J=6.31 Hz, 1 H) 7.01-7.55 (m, 8 H) 8.37 (s, 1 H), [M+H]⁺ 439.6.

General Procedure for Making Ureas from 8-(2-chlorophenyl)-9-(4-chlorophenyl)-N-(piperidin-4-yl)-9H-purin-6-amine To a solution of 8-(2-chlorophenyl)-9-(4-chlorophenyl)-N-(piperidin-4-yl)-9H-purin-6-amine (18.4 mg, 0.042 mmol, 1 eq.) in 2 mL of THF was added triethylamine (0.02 mL, 0.126 mmol, 3 eq.) and the appropriate isocyanate (1.5 eq). The reaction is stirred for 16 h. The reaction was concentrated in vacuo. The crude material was purified by silica gel column chromatography using 0-100% CMA 80/ethyl acetate to yield pure compound.

4-{[8-(2-Chlorophenyl)-9-(4-chlorophenyl)-9H-purin-6-yl]amino}-N-ethylpiperidine-1-carboxamide. Reaction proceeded in 86% yield. ¹H NMR (300 MHz, CHLOROFORM-d) δ ppm 1.09 (t, J=7.21 Hz) 1.34-1.60 (m, 2 H) 2.11 (d, J=12.34 Hz, 2 H) 2.83-3.06 (m, 2 H) 3.13-3.32 (m, 2 H) 3.92 (d, J=13.37 Hz, 2 H) 4.40 (d, J=4.90 Hz, 2 H) 5.80 (d, J=7.82 Hz, 1 H) 7.04-7.51 (m, 8 H) 8.37 (s, 1 H), [M+H]⁺ 510.4.

4-{[8-(2-Chlorophenyl)-9-(4-chlorophenyl)-9H-purin-6-yl]amino}-N-(propan-2-yl)piperidine-1-carboxamide. Reaction proceeded in 91% yield. ¹H NMR (300 MHz, CHLOROFORM-d) δ ppm 1.18 (d, J=6.50 Hz, 6 H) 1.46-1.68 (m, 2 H) 2.19 (d, J=10.55 Hz, 2H) 3.03 (t, J=11.59 Hz, 2 H) 3.89-4.10 (m, 3 H) 4.29 (d, J=7.16 Hz, 1 H) 4.42 (br. s., 1 H) 5.88 (d, J=7.82 Hz, 1 H) 7.13-7.64 (m, 8 H) 8.45 (s, 1 H), [M+H]⁺ 524.7.

4-{[8-(2-Chlorophenyl)-9-(4-chlorophenyl)-9H-purin-6-yl]amino}-N-propylpiperidine-1-carboxamide. Reaction proceeded in 95% yield. ¹H NMR (300 MHz, CHLOROFORM-d) δ ppm 0.86-1.01 (m, 3 H) 1.44-1.67 (m, 4 H) 2.19 (d, J=10.64 Hz, 2 H) 3.05 (t, J=11.73 Hz, 2H) 3.22 (q, J=6.59 Hz, 2 H) 3.92-4.08 (m, 2 H) 4.43 (br. s., 1 H) 4.54 (t, J=5.04 Hz, 1 H) 5.88 (d, J=7.72 Hz, 1 H) 7.09-7.58 (m, 8 H) 8.45 (s, 1 H), [M+H]⁺ 524.8.

N-Butyl-4-{[8-(2-chlorophenyl)-9-(4-chlorophenyl)-9H-purin-6-yl]amino}piperidine-1-carboxamide. Reaction proceeded in 91% yield. ¹H NMR (300 MHz, CHLOROFORM-d) δ ppm 0.79-0.92 (m, 3 H) 1.29 (dq, J=14.75, 7.20 Hz, 2 H) 1.36-1.58 (m, 4 H) 2.11 (d, J=10.64 Hz, 2 H) 2.96 (t, J=11.73 Hz, 2 H) 3.17 (q, J=6.75 Hz, 2 H) 3.81-4.01 (m, 2 H) 4.22-4.51 (m, 2 H) 5.79 (d, J=7.54 Hz, 1 H) 7.01-7.53 (m, 8 H) 8.37 (s, 1 H), [M+H]⁺ 538.4.

1-(4-{[8-(2-Chlorophenyl)-9-(4-chlorophenyl)-9H-purin-6-yl]amino}piperidin-1-yl)ethan-1-one. A solution of 8-(2-chlorophenyl)-9-(4-chlorophenyl)-N-(piperidin-4-yl)-9H-purin-6-amine (19.3 mg, 0.044 mmol, 1 eq.) in 1 mL of acetic anhydride and 1 mL of pyridine was stirred for 16 h. The reaction was concentrated in vacuo. The crude material was purified by silica gel column chromatography using 0-100% ethyl acetate/hexanes to yield 9 mg (43%) of desired 1-(4-{[8-(2-chlorophenyl)-9-(4-chlorophenyl)-9H-purin-6-yl]amino}piperidin-1-yl)ethan-1-one. Compound was determined to be 95% pure by ¹H NMR. ¹H NMR (300 MHz, CHLOROFORM-d) δ ppm 1.36-1.52 (m, 2 H) 2.03-2.27 (m, 5 H) 2.81 (t, J=11.49 Hz, 1 H) 3.13-3.33 (m, 1 H) 3.81 (d, J=13.75 Hz, 1 H) 4.41 (br. s., 1 H) 4.55 (d, J=13.66 Hz, 1 H) 5.78 (br. s., 1 H) 7.00-7.55 (m, 8 H) 8.37 (s, 1 H), [M+Na]⁺ 503.8.

8-(2-Chlorophenyl)-9-(4-chlorophenyl)-N-(1-methanesulfonylpiperidin-4-yl)-9H-purin-6-amine. To a solution of 8-(2-chlorophenyl)-9-(4-chlorophenyl)-N-(piperidin-4-yl)-9H-purin-6-amine (18.4 mg, 0.042 mmol, 1 eq.) in 2 mL of THF was added methanesulfonyl chloride (0.005 mL, 0.063 mmol, 1.5 eq.) and triethylamine (0.02 mL, 0.126 mmol, 3 eq.). The mixture was stirred for 16 h. The reaction was concentrated in vacuo. The crude material was purified by silica gel column chromatography using 0-100% ethyl acetate/hexanes to yield 20 mg (91%) of 8-(2-chlorophenyl)-9-(4-chlorophenyl)-N-(1-methanesulfonylpiperidin-4-yl)-9H-purin-6-amine. ¹H NMR (300 MHz, CHLOROFORM-d) δ ppm 1.58-1.76 (m, 2 H) 2.21 (d, J=10.64 Hz, 2 H) 2.76 (s, 3 H) 2.90 (t, J=10.93 Hz, 2 H) 3.77 (d, J=12.15 Hz, 2 H) 4.33 (br. s., 1 H) 5.84 (br. s., 1 H) 7.04-7.51 (m, 8 H) 8.36 (s, 1 H), [M−H]⁻ 515.7.

tert-Butyl (3R)-3-{[8-(2-chlorophenyl)-9-(4-chlorophenyl)-9H-purin-6-yl]amino}piperidine-1-carboxylate. To a solution of 6-chloro-8-(2-chlorophenyl)-9-(4-chlorophenyl)-9H-purine (100 mg, 0.267 mmol, 1 eq.) in 3 mL of ethanol was added tert-butyl (3R)-3-aminopiperidine-1-carboxylate (64 mg, 0.32 mmol, 1.2 eq.) and triethylamine (0.06 mL, 0.4 mmol, 1.5 eq.). The reaction was heated to 80° C. for 16 h. The reaction was concentrated in vacuo. The crude material was purified by silica gel column chromatography using 0-100% ethyl acetate/hexanes to yield 124 mg (86%) of tert-butyl (3R)-3-{[8-(2-chlorophenyl)-9-(4-chlorophenyl)-9H-purin-6-yl]amino}piperidine-1-carboxylate. $^1$H NMR (300 MHz, CHLOROFORM-d) δ ppm 1.33 (br. s., 9 H) 1.49-1.67 (m, 2 H) 1.74 (d, J=6.97 Hz, 1 H) 2.00 (d, J=2.83 Hz, 1 H) 3.20 (br. s, 2 H) 3.50 (br. s, 1 H) 3.88 (br. s, 1 H) 4.32 (br. s., 1 H) 5.87 (d, J=7.44 Hz, 1 H) 7.02-7.54 (m, 8 H) 8.38 (s, 1 H), [M+H]$^+$ 539.3.

tert-Butyl (3S)-3-{[8-(2-chlorophenyl)-9-(4-chlorophenyl)-9H-purin-6-yl]amino}piperidine-1-carboxylate. To a solution of 6-chloro-8-(2-chlorophenyl)-9-(4-chlorophenyl)-9H-purine (100 mg, 0.267 mmol, 1 eq.) in 3 mL of ethanol was added tert-butyl (3S)-3-aminopiperidine-1-carboxylate (64 mg, 0.32 mmol, 1.2 eq.) and triethylamine (0.06 mL, 0.4 mmol, 1.5 eq.). The reaction was heated to 80° C. for 16 h. The reaction was concentrated in vacuo. The crude material was purified by silica gel column chromatography using 0-100% ethyl acetate/hexanes to yield 137 mg (95%) of tert-butyl (3S)-3-{[8-(2-chlorophenyl)-9-(4-chlorophenyl)-9H-purin-6-yl]amino}piperidine-1-carboxylate. $^1$H NMR (300 MHz, CHLOROFORM-d) δ ppm 1.43 (br. s., 9 H) 1.60-1.76 (m, 2 H) 1.77-1.93 (m, 1 H) 2.08-2.22 (m, 1 H) 3.30 (br. s., 2 H) 3.60 (br. s., 1H) 3.98 (br. s., 1 H) 4.42 (br. s., 1 H) 5.96 (d, J=7.54 Hz, 1 H) 7.14-7.68 (m, 8 H) 8.48 (s, 1 H), [M+H]$^+$ 539.4.

8-(2-chlorophenyl)-9-(4-chlorophenyl)-N-[(3R)-piperidin-3-yl]-9H-purin-6-amine. A solution of tert-butyl (3R)-3-{[8-(2-chlorophenyl)-9-(4-chlorophenyl)-9H-purin-6-yl]amino}piperidine-1-carboxylate (109 mg, 0.202 mmol) was stirred in dichloromethane (7 mL) and trifluoroacetic acid (3 mL) for 16 h. The reaction was concentrated in vacuo. The crude product was dissolved in ethyl acetate and washed with saturated NaHCO$_3$. The aqueous layer was extracted twice with ethyl acetate. The combined organic layer was washed with brine and dried with MgSO$_4$. The crude material was purified by silica gel column chromatography using 0-100% CMA 80/ethyl acetate to yield 70 mg (79%) of 8-(2-chlorophenyl)-9-(4-chlorophenyl)-N-[(3R)-piperidin-3-yl]-9H-purin-6-amine. $^1$H NMR (300 MHz, CHLOROFORM-d) δ ppm 1.43-1.82 (m, 4 H) 1.91-2.03 (m, 1 H) 2.67 (dt, J=11.68, 7.16 Hz, 2 H) 2.76-2.94 (m, 1 H) 3.21 (dd, J=11.82, 2.87 Hz, 1 H) 4.28 (br. s., 1 H) 6.11 (d, J=6.12 Hz, 1 H) 6.98-7.57 (m, 8 H) 8.36 (s, 1 H), [M+H]$^+$ 439.6.

8-(2-chlorophenyl)-9-(4-chlorophenyl)-N-[(3S)-piperidin-3-yl]-9H-purin-6-amine. A solution of tert-butyl (3S)-3-{[8-(2-chlorophenyl)-9-(4-chlorophenyl)-9H-purin-6-yl]amino}piperidine-1-carboxylate (120 mg, 0.22 mmol) was stirred in dichloromethane (7 mL) and trifluoroacetic acid (3 mL) for 16 h. The reaction was concentrated in vacuo. The crude product was dissolved in ethyl acetate and washed with saturated NaHCO$_3$. The aqueous layer was extracted twice with ethyl acetate. The combined organic layer was washed with brine and dried with MgSO$_4$. The crude material was purified by silica gel column chromatography using 0-100% CMA 80/ethyl acetate to yield 64 mg (65%) of 8-(2-chlorophenyl)-9-(4-chlorophenyl)-N-[(3S)-piperidin-3-yl]-9H-purin-6-amine. $^1$H NMR (300 MHz, CHLOROFORM-d) δ ppm 1.55-1.86 (m, 4 H) 2.01-2.14 (m, 1 H) 2.66-2.85 (m, 2 H) 2.87-3.04 (m, 1 H) 3.32 (dd, J=11.77, 2.35 Hz, 1 H) 4.39 (br. s., 1 H) 6.20 (d, J=5.84 Hz, 1 H) 7.12-7.66 (m, 8 H) 8.47 (s, 1 H), [M+H]$^+$ 439.6.

8-(2-chlorophenyl)-9-(4-chlorophenyl)-N-[(3R)-1-methanesulfonylpiperidin-3-yl]-9H-purin-6-amine. To a solution of 8-(2-chlorophenyl)-9-(4-chlorophenyl)-N-[(3R)-piperidin-3-yl]-9H-purin-6-amine (20 mg, 0.046 mmol, 1 eq.) in 2 mL of dichloromethane was added methanesulfonyl chloride (0.007 mL, 0.091 mmol, 2 eq.) and triethylamine (0.02 mL, 0.137 mmol, 3 eq.). The mixture was stirred for 16 h. The reaction was concentrated in vacuo. The crude material was purified by silica gel column chromatography using 0-100% ethyl acetate/hexanes to yield 12 mg (51%) of 8-(2-chlorophenyl)-9-(4-chlorophenyl)-N-[(3R)-1-methanesulfonylpiperidin-3-yl]-9H-purin-6-amine. $^1$H NMR (300 MHz, CHLOROFORM-d) δ ppm 1.81-2.18 (m, 4 H) 2.77-2.94 (m, 3 H) 3.07-3.29 (m, 2 H) 3.42 (br. s., 1 H) 3.82 (d, J=9.89 Hz, 1 H) 4.68 (br. s., 1 H) 6.13 (br. s., 1 H) 7.12-7.65 (m, 8 H) 8.48 (s, 1 H), [M+H]$^+$ 517.8.

1-[(3R)-3-{[8-(2-chlorophenyl)-9-(4-chlorophenyl)-9H-purin-6-yl]amino}piperidin-1-yl]ethan-1-one. A solution of 8-(2-chlorophenyl)-9-(4-chlorophenyl)-N-[(3R)-piperidin-3-yl]-9H-purin-6-amine (20 mg, 0.046 mmol, 1 eq.) in 1 mL of acetic anhydride and 1 mL of pyridine was stirred for 16 h. The reaction was concentrated in vacuo. The crude material was purified by silica gel column chromatography using 0-100% ethyl acetate/hexanes to yield 19 mg (87%) of 1-[(3R)-3-{[8-(2-chlorophenyl)-9-(4-chlorophenyl)-9H-purin-6-yl]amino}piperidin-1-yl]ethan-1-one. $^1$H NMR (300 MHz, CHLOROFORM-d) δ ppm 1.53-1.92 (m, 3 H) 2.07 (br. s., 4 H) 2.84-3.37 (m, 2 H) 3.86-4.59 (m, 3 H) 5.88 (br. s., 1 H) 7.04-7.60 (m, 8 H) 8.37 (br. s., 1 H), [M+H]$^+$ 481.3.

(3R)-3-{[8-(2-chlorophenyl)-9-(4-chlorophenyl)-9H-purin-6-yl]amino}-N-ethylpiperidine-1-carboxamide. To a solution of 8-(2-chlorophenyl)-9-(4-chlorophenyl)-N-[(3R)-piperidin-3-yl]-9H-purin-6-amine (20 mg, 0.046 mmol, 1 eq.) in 2 mL of THF was added triethylamine (0.02 mL, 0.137 mmol, 3 eq.) and ethyl isocyanate (0.005 mL, 0.068 mmol, 1.5 eq). The reaction is stirred for 16 h. The reaction was concentrated in vacuo. The crude material was purified by silica gel column chromatography using 0-100% ethyl acetate/hexanes to yield 15 mg (65%) of (3R)-3-{[8-(2-chlorophenyl)-9-(4-chlorophenyl)-9H-purin-6-yl]amino}-N-ethylpiperidine-1-carboxamide. $^1$H NMR (300 MHz, CHLOROFORM-d) δ ppm 1.03-1.34 (m, 3 H) 1.56-1.96 (m, 4 H) 2.18 (br. s., 1 H) 3.07 (br. s., 2 H) 3.32 (br. s., 1 H) 3.73-4.42 (m, 3 H) 5.05 (br. s., 1H) 6.02 (d, J=5.84 Hz, 1 H) 7.09-7.63 (m, 8 H) 8.45 (br. s., 1 H), [M+H]$^+$ 510.3.

8-(2-chlorophenyl)-9-(4-chlorophenyl)-N-[(3S)-1-methanesulfonylpiperidin-3-yl]-9H-purin-6-amine. To a solution of 8-(2-chlorophenyl)-9-(4-chlorophenyl)-N-[(3S)-piperidin-3-yl]-9H-purin-6-amine (15.3 mg, 0.035 mmol, 1 eq.) in 2 mL of THF was added methanesulfonyl chloride (0.005 mL, 0.07 mmol, 2 eq.) and triethylamine (0.015 mL, 0.11 mmol, 3 eq.). The mixture was stirred for 16 h. The reaction was concentrated in vacuo. The crude material was purified by silica gel column chromatography using 0-100% ethyl acetate/hexanes to yield 16 mg (89%) of 8-(2-chlorophenyl)-9-(4-chlorophenyl)-N-[(3S)-1-methanesulfonylpiperidin-3-yl]-9H-purin-6-amine. $^1$H NMR (300 MHz, CHLOROFORM-d) δ ppm 1.63-2.02 (m, 4 H) 2.77 (s, 3 H) 2.98-3.19 (m, 2 H) 3.31 (br. s., 1 H) 3.71 (d, J=10.55 Hz, 1 H) 4.56 (br. s., 1 H) 6.01 (d, J=7.54 Hz, 1 H) 6.97-7.56 (m, 8 H) 8.37 (s, 1 H), [M+H]$^+$ 517.4.

1-[(3S)-3-{[8-(2-chlorophenyl)-9-(4-chlorophenyl)-9H-purin-6-yl]amino}piperidin-1-yl]ethan-1-one. A solution of 8-(2-chlorophenyl)-9-(4-chlorophenyl)-N-[(3S)-piperidin-3-yl]-9H-purin-6-amine (15.7 mg, 0.036 mmol, 1 eq.) in 1 mL of acetic anhydride and 1 mL of pyridine was stirred for 16 h. The reaction was concentrated in vacuo. The crude material was purified by silica gel column chromatography using 0-100% ethyl acetate/hexanes to yield 14 mg (81%) of 1-[(3S)-3-{[8-(2-chlorophenyl)-9-(4-chlorophenyl)-9H-purin-6-yl]amino}piperidin-1-yl]ethan-1-one. $^1$H NMR (300 MHz, CHLOROFORM-d) δ ppm 1.48-1.91 (m, 3 H) 2.07 (s, 4 H) 2.90-3.39 (m, 2 H) 3.96-4.57 (m, 3 H) 5.83 (d, J=6.50 Hz, 1 H) 7.04-7.56 (m, 8 H) 8.37 (s, 1 H), [M+H]$^+$ 481.3.

(3S)-3-{[8-(2-chlorophenyl)-9-(4-chlorophenyl)-9H-purin-6-yl]amino}-N-ethylpiperidine-1-carboxamide. To a solution of 8-(2-chlorophenyl)-9-(4-chlorophenyl)-N-[(3S)-piperidin-3-yl]-9H-purin-6-amine (16 mg, 0.036 mmol, 1 eq.) in 2 mL of THF was added triethylamine (0.015 mL, 0.109 mmol, 3 eq.) and ethyl isocyanate (0.004 mL, 0.055 mmol, 1.5 eq). The reaction is stirred for 16 h. The reaction was concentrated in vacuo. The crude material was purified by silica gel column chromatography using 0-100% ethyl acetate/hexanes to yield 16 mg (86%) of (3S)-3-{[8-(2-chlorophenyl)-9-(4-chlorophenyl)-9H-purin-6-yl]amino}-N-ethylpiperidine-1-carboxamide. $^1$H NMR (300 MHz, CHLOROFORM-d) δ ppm 1.06-1.34 (m, 3 H) 1.53-1.95 (m, 4 H) 2.12-2.29 (m, 1 H) 3.07 (br. s., 2 H) 3.32 (br. s., 1 H) 3.72-4.41 (m, 3 H) 5.06 (br. s., 1 H) 6.02 (d, J=6.12 Hz, 1 H) 7.08-7.66 (m, 8 H) 8.45 (br. s., 1 H), [M+H]$^+$ 510.3.

tert-Butyl N-{1-[8-(2-chlorophenyl)-9-(4-chlorophenyl)-9H-purin-6-yl]piperidin-4-yl}carbamate. To a solution of 6-chloro-8-(2-chlorophenyl)-9-(4-chlorophenyl)-9H-purine (309 mg, 0.824 mmol, 1 eq.) in 10 mL of ethanol was added tert-butyl N-(piperidin-4-yl)carbamate (329 mg, 1.65 mmol, 2 eq.). The reaction was heated to 80° C. for 16 h. The reaction was concentrated in vacuo. The crude material was purified by silica gel column chromatography using 0-100% ethyl acetate/hexanes to yield 442 mg (99%) of tert-butyl N-{1-[8-(2-chlorophenyl)-9-(4-chlorophenyl)-9H-purin-6-yl]piperidin-4-yl}carbamate. $^1$H NMR (300 MHz, CHLOROFORM-d) δ ppm 1.40-1.53 (m, 11 H) 2.12 (d, J=11.40 Hz, 2 H) 3.32 (t, J=11.63 Hz, 2 H) 3.80 (br. s., 1 H) 4.41-4.68 (m, 1 H) 5.40 (br. s., 2 H) 7.16-7.24 (m, 2 H) 7.26-7.43 (m, 5 H) 7.51 (d, J=6.59 Hz, 1 H) 8.38 (s, 1 H), [M+H]$^+$ 539.2.

1-[8-(2-chlorophenyl)-9-(4-chlorophenyl)-9H-purin-6-yl]piperidin-4-amine. A solution of tert-butyl N-{1-[8-(2-chlorophenyl)-9-(4-chlorophenyl)-9H-purin-6-yl]piperidin-4-yl}carbamate (380 mg, 0.705 mmol) was stirred in dichloromethane (7 mL) and trifluoroacetic acid (3 mL) for 16 h. The reaction was concentrated in vacuo. The crude product was dissolved in ethyl acetate and washed with saturated NaHCO$_3$. The aqueous layer was extracted twice with ethyl acetate. The combined organic layer was washed with brine and dried with MgSO$_4$. The crude material was purified by silica gel column chromatography using 0-100% CMA 80/ethyl acetate to yield 294 mg (95%) of 1-[8-(2-chlorophenyl)-9-(4-chlorophenyl)-9H-purin-6-yl]piperidin-4-amine. Compound was determined to be 95% pure by $^1$H NMR and was carried forward into further chemistry. $^1$H NMR (300 MHz, CHLOROFORM-d) δ ppm 1.31-1.54 (m, 2 H) 1.92-2.08 (m, 2 H) 2.92-3.12 (m, 1 H) 3.27 (t, J=11.87 Hz, 2 H) 5.42 (br. s., 2 H) 7.07-7.61 (m, 8 H) 8.38 (s, 1H), [M+H]$^+$ 439.4.

General Procedure for Making Ureas from tert-butyl N-{1-[8-(2-chlorophenyl)-9-(4-chlorophenyl)-9H-purin-6-yl]piperidin-4-yl}carbamate To a solution of tert-butyl N-{1-[8-(2-chlorophenyl)-9-(4-chlorophenyl)-9H-purin-6-yl]piperidin-4-yl}carbamate (20 mg, 0.046 mmol, 1 eq.) in 2 mL of THF was added triethylamine (0.02 mL, 0.136 mmol, 3 eq.) and the appropriate isocyanate (1.5 eq). The reaction is stirred for 16 h. The reaction was concentrated in vacuo. The crude material was purified by silica gel column chromatography using 0-100% ethyl acetate/hexane to yield pure compound.

1-{1-[8-(2-chlorophenyl)-9-(4-chlorophenyl)-9H-purin-6-yl]piperidin-4-yl}-3-ethylurea. Reaction proceeded in 56% yield. $^1$H NMR (300 MHz, CHLOROFORM-d) δ ppm 1.13 (t, J=7.21 Hz, 3 H) 1.33-1.57 (m, 2 H) 2.04-2.20 (m, 2 H) 3.14-3.25 (m, 2 H) 3.32 (t, J=12.06 Hz, 2 H) 3.86-4.05 (m, 1 H) 4.23-4.45 (m, 2 H) 5.39 (br. s., 2 H) 7.03-7.59 (m, 8 H) 8.37 (s, 1 H), [M+H]$^+$ 510.2.

1-{1-[8-(2-chlorophenyl)-9-(4-chlorophenyl)-9H-purin-6-yl]piperidin-4-yl}-3-(propan-2-yl)urea. Reaction proceeded in 84% yield. $^1$H NMR (300 MHz, CHLOROFORM-d) δ ppm 1.14 (d, J=6.50 Hz, 6 H) 1.35-1.55 (m, 2 H) 2.12 (d, J=10.46 Hz, 2 H) 3.32 (t, J=12.10 Hz, 2 H) 3.84 (dd, J=13.66, 6.69 Hz, 1 H) 3.89-4.04 (m, 1 H) 4.12-4.36 (m, 2 H) 5.39 (br. s., 2 H) 7.19 (d, J=8.67 Hz, 2 H) 7.28-7.43 (m, 5 H) 7.51 (d, J=6.69 Hz, 1 H) 8.37 (s, 1 H), [M+H]$^+$ 524.6.

1-{1-[8-(2-chlorophenyl)-9-(4-chlorophenyl)-9H-purin-6-yl]piperidin-4-yl}-3-propylurea. Reaction proceeded in 71% yield. $^1$H NMR (300 MHz, CHLOROFORM-d) δ ppm 0.83-0.98 (m, 3 H) 1.37-1.59 (m, 4 H) 2.13 (d, J=10.27 Hz, 2 H) 3.12 (q, J=6.66 Hz, 2 H) 3.32 (t, J=12.01 Hz, 2 H) 3.83-4.07 (m, 1 H) 4.20-4.47 (m, 2 H) 5.40 (br. s., 2 H) 7.13-7.24 (m, 2 H) 7.28-7.44 (m, 5 H) 7.51 (d, J=6.69 Hz, 1 H) 8.37 (s, 1 H), [M+H]$^+$ 524.1.

3-butyl-1-{1-[8-(2-chlorophenyl)-9-(4-chlorophenyl)-9H-purin-6-yl]piperidin-4-yl}urea. Reaction proceeded in 69% yield. $^1$H NMR (300 MHz, CHLOROFORM-d) δ ppm 0.84-0.99 (m, 3 H) 1.28-1.55 (m, 6 H) 2.04-2.20 (m, 2 H) 3.15 (q, J=6.75 Hz, 2 H) 3.32 (t, J=12.15 Hz, 2 H) 3.83-4.08 (m, 1 H) 4.18-4.39 (m, 2 H) 5.40 (br. s., 2 H) 7.08-7.43 (m, 7 H) 7.51 (d, J=6.69 Hz, 1 H) 8.37 (s, 1 H), [M+H]$^+$ 538.4.

General Procedure for Making Sulfonamides from tert-butyl N-{1-[8-(2-chlorophenyl)-9-(4-chlorophenyl)-9H-purin-6-yl]piperidin-4-yl}-carbamate To a solution of tert-butyl N-{1-[8-(2-chlorophenyl)-9-(4-chlorophenyl)-9H-purin-6-yl]piperidin-4-yl}carbamate (21 mg, 0.048 mmol, 1 eq.) in 2 mL of THF was added triethylamine (0.02 mL, 0.143 mmol, 3 eq.) and the appropriate sulfonyl chloride (2 eq). The reaction is stirred for 16 h. The reaction was concentrated in vacuo. The crude material was purified by silica gel column chromatography using 0-100% ethyl acetate/hexane to yield pure compound.

N-{1-[8-(2-chlorophenyl)-9-(4-chlorophenyl)-9H-purin-6-yl]piperidin-4-yl}methanesulfonamide. Reaction proceeded in 32% yield. $^1$H NMR (300 MHz, CHLOROFORM-d) δ ppm 1.55-1.67 (m, 2 H) 2.18 (d, J=12.53 Hz, 2 H) 3.03 (s, 3 H) 3.36 (t, J=12.29 Hz, 2 H) 3.59-3.80 (m, 1 H) 4.31 (d, J=7.44 Hz, 1 H) 5.43 (d, J=9.89 Hz, 2 H) 7.13-7.44 (m, 7 H) 7.51 (d, J=6.78 Hz, 1 H) 8.39 (s, 1 H), [M+H]$^+$ 517.6.

N-{1-[8-(2-chlorophenyl)-9-(4-chlorophenyl)-9H-purin-6-yl]piperidin-4-yl}benzenesulfonamide. Reaction proceeded in 53% yield. $^1$H NMR (300 MHz, CHLOROFORM-d) δ ppm 1.43-1.59 (m, 2 H) 1.94 (d, J=10.46 Hz, 2 H) 3.30 (t, J=11.96 Hz, 2H) 3.41-3.66 (m, 1 H) 4.62 (d, J=7.54 Hz, 1 H) 5.26 (d, J=10.08 Hz, 2 H) 7.07-7.69 (m, 10 H) 7.92 (d, J=7.35 Hz, 2 H) 8.35 (s, 1 H), [M+H]$^+$ 579.4.

N-{1-[8-(2-chlorophenyl)-9-(4-chlorophenyl)-9H-purin-6-yl]piperidin-4-yl}aminosulfonamide. To a solution of 1-[8-(2-chlorophenyl)-9-(4-chlorophenyl)-9H-purin-6-yl]piperidin-4-amine (36.6 mg, 0.083 mmol, 1 eq.) in 2 mL of dioxane was added sulfamide (40 mg, 0.42 mmol, 5 eq.). The reaction was heated to 80° C. for 16 h. The reaction was concentrated in vacuo. The crude material was purified by silica gel column chromatography using 0-100% ethyl acetate/hexane to yield 34 mg (79%) of desired compound. $^1$H NMR (300 MHz, METHANOL-d$_4$) δ ppm 1.51-1.72 (m, 2 H) 2.15 (br. s., 2 H) 3.38-3.52 (m, 2 H) 3.54-3.65 (m, 1 H) 5.18-5.41 (m, 2 H) 7.24-7.50 (m, 7 H) 7.54-7.67 (m, 1 H) 8.23 (s, 1 H), [M+H]$^+$ 518.5.

N-{1-[8-(2-chlorophenyl)-9-(4-chlorophenyl)-9H-purin-6-yl]piperidin-4-yl}-1,1,1-trifluoromethanesulfonamide. To a solution of 1-[8-(2-chlorophenyl)-9-(4-chlorophenyl)-9H-purin-6-yl]piperidin-4-amine (27.9 mg, 0.064 mmol, 1 eq.) in 2 mL of dichloromethane was added triethylamine (0.027 mL, 0.191 mmol, 3 eq.) and the trifluoromethanesulfonic anhydride (0.01 mL, 0.069 mmol, 1 eq.). The reaction is stirred for 16 h. The reaction was concentrated in vacuo. The crude material was purified by silica gel column chromatography using 0-100% ethyl acetate/hexane to yield 9 mg (25%) of desired compound. $^1$H NMR (300 MHz, CHLOROFORM-d) δ ppm 1.60-1.76 (m, 2 H) 2.20 (d, J=12.62 Hz, 2 H) 3.30 (t, J=12.57 Hz, 2 H) 3.71-3.92 (m, 1 H) 4.95 (d, J=8.48 Hz, 1 H) 5.50 (d, J=12.34 Hz, 2 H) 7.14-7.43 (m, 7 H) 7.50 (d, J=6.97 Hz, 1 H) 8.39 (s, 1 H) [M+H]$^+$ 571.7.

General Procedure for Making Amides from tert-butyl N-{1-[8-(2-chlorophenyl)-9-(4-chlorophenyl)-9H-purin-6-yl]piperidin-4-yl}carbamate To a solution of tert-butyl N-{1-[8-(2-chlorophenyl)-9-(4-chlorophenyl)-9H-purin-6-yl]piperidin-4-yl}carbamate (21 mg, 0.048 mmol, 1 eq.) in 2 mL of THF was added triethylamine (0.02 mL, 0.143 mmol, 3 eq.) and the appropriate anhydride (2 eq). The reaction is stirred for 16 h. The reaction was concentrated in vacuo. The crude material was purified by silica gel column chromatography using 0-100% ethyl acetate/hexane to yield pure compound.

N-{1-[8-(2-Chlorophenyl)-9-(4-chlorophenyl)-9H-purin-6-yl]piperidin-4-yl}acetamide. Reaction proceeded in 65% yield. $^1$H NMR (300 MHz, CHLOROFORM-d) δ ppm 1.42-1.56 (m, 2 H) 1.99 (s, 3 H) 2.12 (d, J=10.08 Hz, 2 H) 3.30 (t, J=12.24 Hz, 2 H) 4.09-4.25 (m, 1 H) 5.41 (d, J=8.01 Hz, 3 H) 7.13-7.43 (m, 7 H) 7.51 (d, J=6.78 Hz, 1 H) 8.38 (s, 1 H), [M+H]$^+$ 481.4.

N-{1-[8-(2-Chlorophenyl)-9-(4-chlorophenyl)-9H-purin-6-yl]piperidin-4-yl}-2,2,2-trifluoroacetamide. Reaction proceeded in 39% yield. $^1$H NMR (300 MHz, CHLOROFORM-d) δ ppm 1.62 (qd, J=11.99, 3.86 Hz, 2 H) 2.18 (d, J=10.83 Hz, 2 H) 3.31 (t, J=12.43 Hz, 2 H) 4.11-4.29 (m, 1 H) 5.53 (br. s., 2 H) 6.19 (d, J=7.06 Hz, 1 H) 7.01-7.57 (m, 8 H) 8.40 (s, 1 H), [M+H]$^+$ 535.4.

N-{1-[8-(2-Chlorophenyl)-9-(4-chlorophenyl)-9H-purin-6-yl]piperidin-4-yl}benzamide. Reaction proceeded in 19% yield. $^1$H NMR (300 MHz, CHLOROFORM-d) δ ppm 1.82-1.97 (m, 2 H) 2.77 (d, J=12.34 Hz, 2 H) 3.08 (br. s., 2 H) 3.46-3.62 (m, 1 H) 3.66-3.80 (m, 1 H) 4.01-4.13 (m, 1 H) 5.26-5.46 (m, 1 H) 7.12-7.59 (m, 13 H) 8.38 (s, 1 H), [M+H]$^+$ 543.6.

General Procedure for Making Amides from 1-[8-(2-chlorophenyl)-9-(4-chlorophenyl)-9H-purin-6-yl]-4-phenylpiperidin-4-amine To a solution of 1-[8-(2-chlorophenyl)-9-(4-chlorophenyl)-9H-purin-6-yl]piperidin-4-amine (22 mg, 0.05 mmol, 1 eq.) in 2 mL of THF was added triethylamine (0.02 mL, 0.143 mmol, 3 eq.), (benzotriazol-1-yloxy)tris(dimethylamino)phosphonium hexafluorophosphate (BOP) (22 mg, 0.05 mmol, 1 eq.), and the appropriate carboxylic acid (1 eq). The reaction was stirred for 16 h. The reaction was concentrated in vacuo. The crude material was purified by silica gel column chromatography using 0-100% ethyl acetate/hexane to yield compound. The product was purified further by dissolving in ethyl acetate and precipitating with hexane. The solid, pure compound was collected.

N-{1-[8-(2-Chlorophenyl)-9-(4-chlorophenyl)-9H-purin-6-yl]piperidin-4-yl}cyclohexanecarboxamide. Reaction proceeded in >99% yield. $^1$H NMR (300 MHz, CHLOROFORM-d) δ ppm 1.15-2.17 (m, 14 H) 2.23-2.40 (m, 1 H) 3.31 (t, J=12.20 Hz, 2 H) 4.05-4.25 (m, 1 H) 5.22-5.61 (m, 3 H) 7.14-7.42 (m, 7 H) 7.51 (d, J=6.69 Hz, 1 H) 8.38 (s, 1H), [M+H]$^+$ 549.5.

N-{1-[8-(2-Chlorophenyl)-9-(4-chlorophenyl)-9H-purin-6-yl]piperidin-4-yl}pentanamide. Reaction proceeded in >99% yield. $^1$H NMR (300 MHz, CHLOROFORM-d) δ ppm 0.84-0.98 (m, 3 H) 1.27-1.75 (m, 5 H) 2.05-2.23 (m, 3 H) 2.26-2.44 (m, 1 H) 3.31 (t, J=12.24 Hz, 2 H) 4.02-4.30 (m, 1 H) 5.22-5.63 (m, 3 H) 7.13-7.44 (m, 7 H) 7.51 (d, J=6.78 Hz, 1 H) 8.38 (s, 1H), [M+H]$^+$ 523.5.

N-{1-[8-(2-Chlorophenyl)-9-(4-chlorophenyl)-9H-purin-6-yl]piperidin-4-yl}-2-cyclohexylacetamide. Reaction proceeded in >99% yield. $^1$H NMR (300 MHz, CHLOROFORM-d) δ ppm 0.86-1.00 (m, 3 H) 1.05-1.87 (m, 10 H) 2.02-2.18 (m, 4 H) 3.31 (t, J=12.10 Hz, 2 H) 4.10-4.28 (m, 1 H) 5.22-5.62 (m, 3 H) 7.14-7.43 (m, 7 H) 7.51 (d, J=6.78 Hz, 1 H) 8.38 (s, 1 H), [M+H]$^+$ 562.2.

N-{1-[8-(2-Chlorophenyl)-9-(4-chlorophenyl)-9H-purin-6-yl]piperidin-4-yl}-3-methylbutanamide. Reaction proceeded in >99% yield. $^1$H NMR (300 MHz, CHLOROFORM-d) δ ppm 0.97 (dd, J=9.94, 6.45 Hz, 6 H) 1.50 (qd, J=11.85, 3.81 Hz, 1 H) 2.01-2.17 (m, 4 H) 2.19-2.27 (m, 2 H) 3.31 (t, J=12.24 Hz, 2 H) 4.10-4.27 (m, 1 H) 5.39 (d, J=8.01 Hz, 3 H) 7.14-7.42 (m, 7 H) 7.51 (d, J=6.78 Hz, 1 H) 8.38 (s, 1 H), [M+H]$^+$ 523.3.

N-{1-[8-(2-Chlorophenyl)-9-(4-chlorophenyl)-9H-purin-6-yl]piperidin-4-yl}cyclopentanecarboxamide. Reaction proceeded in 86% yield. $^1$H NMR (300 MHz, CHLOROFORM-d) δ ppm 1.39-1.99 (m, 9 H) 2.06-2.21 (m, 3 H) 2.41-2.58 (m, 1 H) 3.31 (t, J=12.24 Hz, 2 H) 4.08-4.27 (m, 1 H) 5.40 (d, J=7.91 Hz, 3 H) 7.12-7.42 (m, 7 H) 7.51 (d, J=6.78 Hz, 1 H) 8.38 (s, 1 H), [M+H]$^+$ 535.5.

N-{1-[8-(2-Chlorophenyl)-9-(4-chlorophenyl)-9H-purin-6-yl]piperidin-4-yl}-4-methylpentanamide. Reaction ceeded in 82% yield. $^1$H NMR (300 MHz, CHLOROFORM-d) δ ppm 0.85-0.95 (m, 6 H) 1.40-1.62 (m, 5 H) 2.03-2.23 (m, 3 H) 2.34 (t, J=7.54 Hz, 1 H) 3.31 (t, J=12.24 Hz, 2 H) 4.08-4.29 (m, 1 H) 5.42 (d, J=7.91 Hz, 3 H) 7.14-7.43 (m, 7 H) 7.51 (d, J=7.16 Hz, 1 H) 8.38 (s, 1 H), [M+H]$^+$ 537.5.

N-{1-[8-(2-Chlorophenyl)-9-(4-chlorophenyl)-9H-purin-6-yl]piperidin-4-yl}-2-cyclopentylacetamide. Reaction proceeded in 98% yield. $^1$H NMR (300 MHz, CHLOROFORM-d) δ ppm 1.06-1.23 (m, 3 H) 1.44-1.69 (m, 5 H) 1.74-1.93 (m, 3 H) 2.06-2.28 (m, 3 H) 2.30-2.41 (m, 1 H) 3.32 (t, J=12.20 Hz, 2 H) 4.08-4.29 (m, 1 H) 5.41 (d, J=7.91 Hz, 3 H) 7.14-7.42 (m, 7 H) 7.51 (d, J=6.78 Hz, 1 H) 8.38 (s, 1 H), [M+H]$^+$ 549.5.

General Procedure for Making Amides from 1-[8-(2-chlorophenyl)-9-(4-chlorophenyl)-9H-purin-6-yl]piperidin-4-amine using amino acids To a solution of 1-[8-(2-chlorophenyl)-9-(4-chlorophenyl)-9H-purin-6-yl]piperidin-4-amine (22 mg, 0.05 mmol, 1 eq.) in 2 mL of THF was added triethylamine (0.02 mL, 0.143 mmol, 3 eq.), (benzotriazol-1-yloxy)tris(dimethylamino)phosphonium hexafluorophosphate (BOP) (22 mg, 0.05 mmol, 1 eq.), and the appropriate carboxylic acid (1 eq). The reaction was stirred for 16 h. The reaction was concentrated in vacuo. The crude material was purified by silica gel column chromatography using 0-100% CMA 80/dichloromethane to yield compound. The product was purified further by dissolving in ethyl acetate, washing with water, and precipitating with hexane. The solid, pure compound was collected.

N-{1-[8-(2-Chlorophenyl)-9-(4-chlorophenyl)-9H-purin-6-yl]piperidin-4-yl}-3-(piperidin-1-yl)propanamide. Reaction proceeded in 41% yield. $^1$H NMR (300 MHz, CHLOROFORM-d) δ ppm 1.52-1.60 (m, 4 H) 1.80 (br. s, 3 H) 1.98-2.14 (m, 3 H) 2.76 (t, J=5.93 Hz, 2 H) 2.93 (br. s, 2 H) 3.30 (br. s, 2 H) 3.40 (br. s, 2 H) 3.56 (br. s, 2 H) 3.97-4.15 (m, 1 H) 5.36-5.59 (m, 2 H) 6.46-6.65 (m, 1 H) 7.15-7.42 (m, 7 H) 7.54 (d, J=7.63 Hz, 1 H) 8.37 (s, 1 H), [M+H]$^+$ 580.6.

N-{1-[8-(2-chlorophenyl)-9-(4-chlorophenyl)-9H-purin-6-yl]piperidin-4-yl}-2-(dimethylamino)acetamide. Reaction proceeded in 11% yield. $^1$H NMR (300 MHz, CHLOROFORM-d) δ ppm 1.50-1.66 (m, 2 H) 2.01-2.13 (m, 2 H) 2.48 (s, 7 H) 2.64 (d, J=9.32 Hz, 1 H) 3.36 (t, J=11.82 Hz, 2 H) 4.05-4.26 (m, 1 H) 5.41 (br. s., 2 H) 7.08 (d, J=8.19 Hz, 1 H) 7.14-7.42 (m, 7 H) 7.51 (d, J=6.78 Hz, 1 H) 8.37 (s, 1 H), [M+H]$^+$ 524.7.

General Procedure for Making Carbamates from 1-[8-(2-chlorophenyl)-9-(4-chlorophenyl)-9H-purin-6-yl]piperidin-4-amine To a solution of 1-[8-(2-chlorophenyl)-9-(4-chlorophenyl)-9H-purin-6-yl]piperidin-4-amine (12.5 mg, 0.028 mmol, 1 eq.) in 2 mL of THF was added triethylamine (0.02 mL, 0.143 mmol, 5 eq.) and the appropriate chloroformate (2 eq). The reaction was stirred for 16 h. The reaction was concentrated in vacuo. The crude material was purified by silica gel column chromatography using 0-100% ethyl acetate/hexane to yield pure compound.

Methyl N-{1-[8-(2-chlorophenyl)-9-(4-chlorophenyl)-9H-purin-6-yl]piperidin-4-yl}carbamate. Reaction proceeded in 79% yield. $^1$H NMR (300 MHz, CHLOROFORM-d) δ ppm 1.44-1.55 (m, 2 H) 2.13 (d, J=11.49 Hz, 2 H) 3.34 (t, J=12.24 Hz, 2 H) 3.68 (br. s., 3 H) 3.86 (br. s., 1 H) 4.60 (br. s., 1 H) 5.40 (br. s., 2 H) 7.13-7.45 (m, 7 H) 7.51 (d, J=6.88 Hz, 1 H) 8.38 (s, 1 H), [M+H]$^+$ 497.8.

Ethyl N-{1-[8-(2-chlorophenyl)-9-(4-chlorophenyl)-9H-purin-6-yl]piperidin-4-yl}carbamate. Reaction proceeded in 55% yield. $^1$H NMR (300 MHz, CHLOROFORM-d) δ ppm 1.25 (t, J=6.92 Hz, 3 H) 1.43-1.55 (m, 2 H) 2.13 (d, J=11.21 Hz, 2 H) 3.34 (t, J=12.01 Hz, 2 H) 3.86 (br. s., 1 H) 4.06-4.22 (m, 2 H) 4.58 (br. s., 1 H) 5.39 (br. s., 2 H) 7.14-7.43 (m, 7 H) 7.51 (d, J=6.69 Hz, 1 H) 8.38 (s, 1 H), [M+H]$^+$ 511.3.

Phenyl N-{1-[8-(2-chlorophenyl)-9-(4-chlorophenyl)-9H-purin-6-yl]piperidin-4-yl}-carbamate. Reaction proceeded in 50% yield. $^1$H NMR (300 MHz, CHLOROFORM-d) δ ppm 1.59-1.72 (m, 2 H) 2.22 (d, J=11.40 Hz, 2 H) 3.37 (t, J=12.10 Hz, 2 H) 3.84-4.02 (m, 1 H) 4.99 (d, J=7.72 Hz, 1 H) 5.45 (br. s., 2 H) 7.02-7.45 (m, 12 H) 7.52 (d, J=6.88 Hz, 1 H) 8.40 (s, 1 H), [M+H]$^+$ 559.8.

Example 2

Analysis

All compounds were characterized by H$^1$ NMR and evaluated using a calcium mobilization assay. Each compound was pharmacologically characterized using a functional fluorescent CB1 activated Gαq16-coupled intracellular calcium mobilization assay in CHO-K1 cells as has been previously described and apparent affinity (Ke) values were determined. See Zhang et al., *J. Med. Chem.* 2010, 53, 7048, which is incorporated herein by reference. Further characterization of select compounds was performed using radioligand displacement of [3H]1 and equilibrium dissociation constant (Ki) values were determined. Selectivity of these compounds at CB1 versus CB2 was also determined by obtaining Ki values at either receptor using displacement of [3H]CP55940 in membranes of CHO-K1 cells over-expressing either receptor. Data reported are average values from 3-6 measurements.

Select compounds were chosen for study in radioligand displacement assays using radiolabeled rimonobant, SR141716 ([$^3$H]1). Several of these compounds demonstrated good Ki values in the low nM range, with the thiomorpholine 1,1-dioxide-containing compound having a Ki of 16.8 nM. Selectivity against the CB2 receptor was determined by comparing the compound displacement of radiolabeled CP55940, which is a cannabinoid known to act as a full agonist at both CB1 and CB2 receptors. In general, tested compounds were selective for CB1 over CB2.

TABLE 1

Radioligand displacement data for select compounds

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| (piperidine-carboxamide-phenyl) | 9 | 0.28 | 1.79 | 5507 | 3076.5 | 5.6 ± 2.4% |

TABLE 1-continued

Radioligand displacement data for select compounds

[Structure: 9-(4-chlorophenyl)-8-(2-chlorophenyl)-6-X-purine core]

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| [methanesulfonamidomethyl-cyclohexylmethyl-amino] | 201.00 | 44.5 | 258 | 2230 | 8.6 | >50% |
| [sulfamoylaminomethyl-cyclohexylmethyl-amino] | 549.0 | 94.5 | 355 | 10719 | 30.2 | |
| [thiomorpholine 1,1-dioxide] | 159.00 | 16.8 | 32.1 | 834 | 26.0 | |
| [4-amino-4-phenylpiperidinyl] | 15.89 | | 11 | 1657 | 151 | <1% |
| [4-(methanesulfonamido)-4-phenylpiperidinyl] | 2.85 | | 6.21 | 948 | 153 | <1% |

TABLE 1-continued
Radioligand displacement data for select compounds
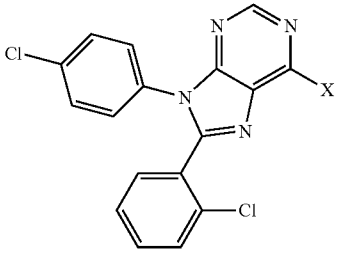
| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| 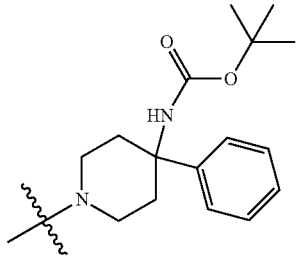 [SMILES: *N1CCC(NC(=O)OC(C)(C)C)(c2ccccc2)CC1] | 3.93 | | 7.12 | 13947 | 1959 | <1% |
| 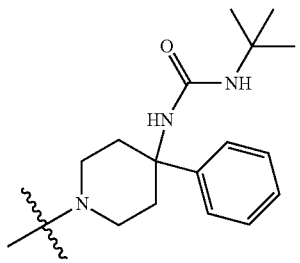 | 19.17 | | 25.5 | 20000 | 784 | <1% |
| 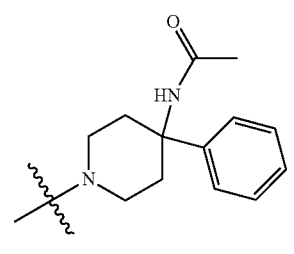 [SMILES: *N1CCC(NC(C)=O)(c2ccccc2)CC1] | 10.31 | | 6 | 726 | 121 | 6% |
|  | 2.2 | | 4.08 | 20000 | 4902 | <1% |

TABLE 1-continued

Radioligand displacement data for select compounds

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| ethyl urea piperidine phenyl | | 443 | 195 | 4645 | 24 | |
| isopropyl urea piperidine phenyl | | 46 | | | | |
| propyl urea piperidine phenyl | | 100 | | | | |
| butyl urea piperidine phenyl | | 62 | | | | |

TABLE 1-continued
Radioligand displacement data for select compounds
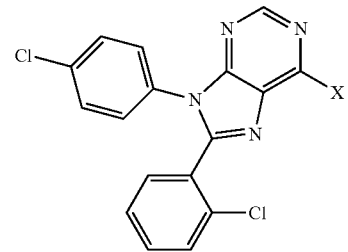
| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
|  | 171 | | | | | |
|  | 199 | | | | | |
|  | 92 | 23.91 | 13599 | 568.8 | | |
|  | Not active | | | | | |
|  | 1148 | | | | | |

TABLE 1-continued

Radioligand displacement data for select compounds

[Structure: 9-(4-chlorophenyl)-8-(2-chlorophenyl)-6-X-9H-purine]

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| [4-(isopropylaminocarbonyl)piperidin-1-yl]amino | 495 | | | | | |
| [4-(propylaminocarbonyl)piperidin-1-yl]amino | 1964 | | | | | |
| [4-(butylaminocarbonyl)piperidin-1-yl]amino | 71 | | | | | |
| [4-acetylpiperidin-1-yl]amino | 19595 | | | | | |
| [4-(methylsulfonyl)piperidin-1-yl]amino | 1645 | | | | | |
| [3-(tert-butoxycarbonyl)piperidin-1-yl]amino | 326 | | | | | |

TABLE 1-continued

Radioligand displacement data for select compounds

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| (N-Boc-3-piperidinyl)amino | 3927 | | | | | |
| (R)-3-piperidinylamino | 5546 | | | | | |
| (S)-3-piperidinylamino | 8406 | | | | | |
| (1-methylsulfonyl-3-piperidinyl)amino | 346 | | | | | |
| (1-acetyl-3-piperidinyl)amino | 920 | | | | | |

TABLE 1-continued

Radioligand displacement data for select compounds

[Structure: purine core with 9-(4-chlorophenyl), 8-(2-chlorophenyl), and 6-X substituents]

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| [3-(ethylcarbamoyl)piperidin-3-ylamino] | 1500 | | | | | |
| [3-(methylsulfonyl)piperidin-3-ylamino] | 6044 | | | | | |
| [3-acetylpiperidin-3-ylamino] | 4449 | | | | | |
| [3-(ethylcarbamoyl)piperidin-3-ylamino] | 1153 | | | | | |
| [4-(Boc-amino)piperidin-1-yl] | 11 | | | | | |

TABLE 1-continued

Radioligand displacement data for select compounds

[Structure: 9-(4-chlorophenyl)-8-(2-chlorophenyl)-6-X-9H-purine core]

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| [methyl carbamate piperidine] | 17 | | | | | |
| [ethyl carbamate piperidine] | 2.3 | 3.57 | | 426 | 119 | |
| [benzamide piperidine] | 4 | 2.55 | | 10649 | 4176 | |
| [4-aminopiperidine] | 316 | | | | | |
| [ethylurea piperidine] | 149 | | | | | |
| [isopropylurea piperidine] | 133 | | | | | |

TABLE 1-continued
Radioligand displacement data for select compounds
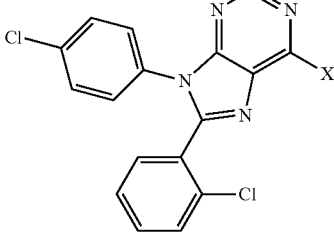
| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| 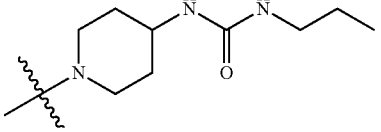 | 132 | | | | | |
| 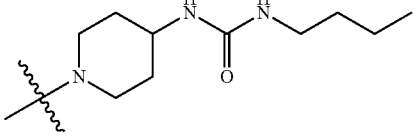 | 49 | | | | | |
| 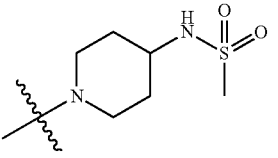 [SMILES: *N1CCC(NS(C)(=O)=O)CC1] | 71 | | | | | |
| 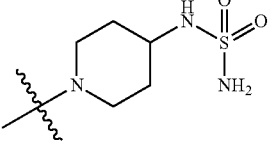 | 2768 | | | | | |
| 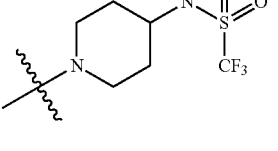 | 1.05 | 6.1 | | 4501 | 738 | |
| 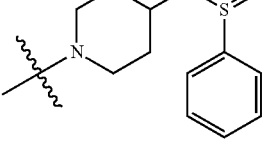 | 0.26 | | | | | |
| 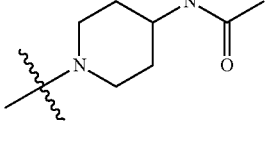 | 631 | | | | | |

TABLE 1-continued
Radioligand displacement data for select compounds
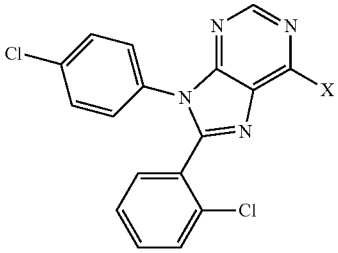
| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| 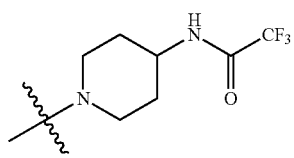 [SMILES: *N1CCC(NC(=O)C(F)(F)F)CC1] | 3.19 | | | | | |
| 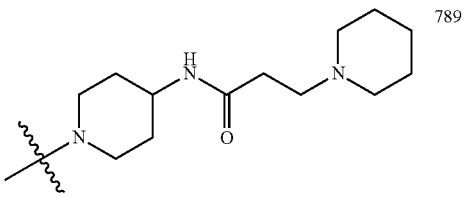 | 789 | | | | | |
| 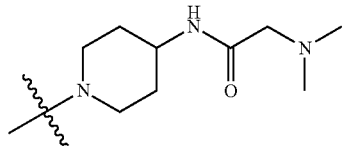 [SMILES: *N1CCC(NC(=O)CN(C)C)CC1] | 140 | | | | | |
| 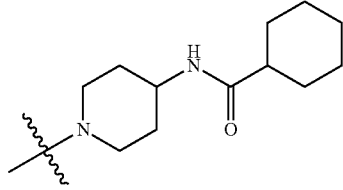 [SMILES: *N1CCC(NC(=O)C2CCCCC2)CC1] | 3.3 | | 3.35 | 835 | 249 | |
| 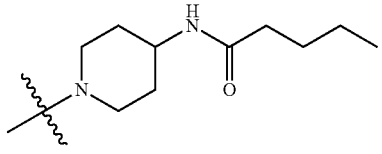 [SMILES: *N1CCC(NC(=O)CCCC)CC1] | 4.9 | | 19.47 | 1046 | 54 | |
| 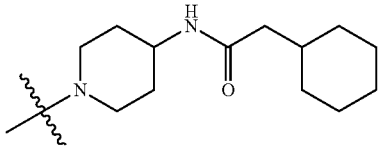 [SMILES: *N1CCC(NC(=O)CC2CCCCC2)CC1] | 2.1 | | 1.93 | 2360 | 1223 | |

TABLE 1-continued

Radioligand displacement data for select compounds

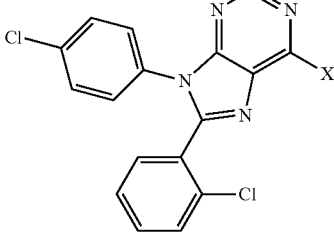

| X | Ke (nM) at CB1 | Ki (nM) v. [3H] SR141716 at CB1 | Ki (nM) v. [3H] CP55940 at CB1 | Ki (nM) v. [3H] CP55940 at CB2 | Binding Selectivity using CP55940 Displacement | % MDCK-MDR transport (Apical to Basal) |
|---|---|---|---|---|---|---|
| 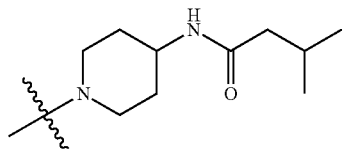 [SMILES: *N1CCC(NC(=O)CC(C)C)CC1] | | 5.4 | 4.01 | 89.5 | 22 | |
| 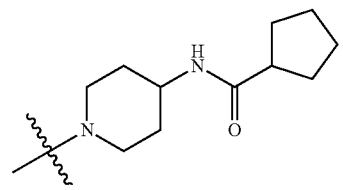 [SMILES: *N1CCC(NC(=O)C2CCCC2)CC1] | | 0.89 | 1.54 | 60.2 | 39 | |
| 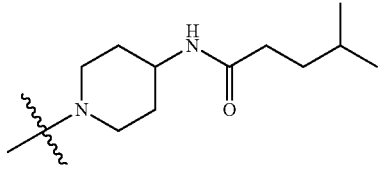 [SMILES: *N1CCC(NC(=O)CCC(C)C)CC1] | | 7.4 | 2.67 | 215 | 81 | |
| 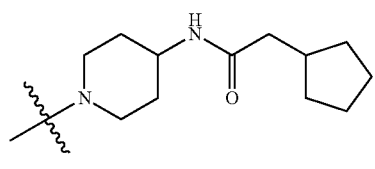 [SMILES: *N1CCC(NC(=O)CC2CCCC2)CC1] | | 2.9 | 2.02 | 569 | 282 | |

The sixth compound entry in the table above is a sulfonamide with a formula weight greater than 500 and a TSPA similar to otenabant. However, unlike otenabant, this sulfonamide is a peripherally selective compound. Oral dosing of this compound at 10 mg/kg in Sprague-Dawley (SD) rats showed good oral absorption (Cmax=1653 ng/g) and limited penetration into the CNS (brain to plasma ratios of 0.05-0.11 were observed).

With regard to the final seven entries (amide compounds) of Table 1, it is noted that alkyl substituents of almost any shape appear to have significant activity at CB1. Binding to the CB2 receptor for certain of these compounds can be modulated by changing the size and shape of the alkyl substituent.

Select compounds were chosen for study to determine penetration into the CNS. Selected compounds were dosed orally at 10 mg/kg in SD rats. Brain and plasma samples were collected at 1, 2, 4, and 24 hours post dose and samples were analyzed by MS (Table 2, below). Since unperfused brains were used and the blood volume in unperfused brains is approximately 4%, a brain to plasma level of ≤0.04 represents no discernible penetration into the CNS.

TABLE 2

Brain Penetration Data for Select Compounds

| Compound | Time | Plasma conc. (ng/mL) | Brain conc. (ng/mL) | Brain/ Plasma |
|---|---|---|---|---|
| 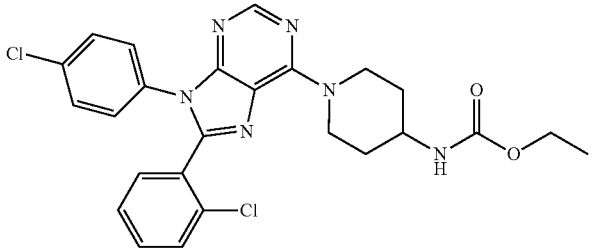 [SMILES: CCOC(=O)NC1CCN(c2ncnc3c2nc(-c2ccccc2Cl)n3-c2ccc(Cl)cc2)CC1] | 1<br>2<br>4<br>24 | 740<br>971<br>1750<br>72.6 | 207<br>132<br>276<br>33.5 | 0.28<br>0.14<br>0.16<br>0.46 |
| 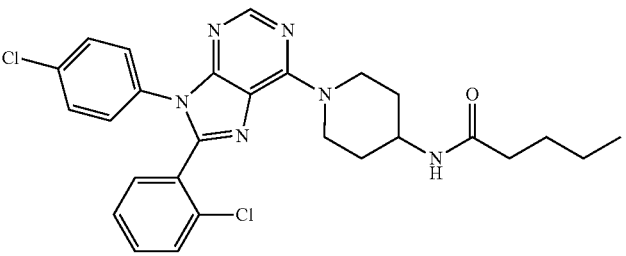 [SMILES: CCCCC(=O)NC1CCN(c2ncnc3c2nc(-c2ccccc2Cl)n3-c2ccc(Cl)cc2)CC1] | 1<br>2<br>4<br>24 | 1430<br>2780<br>1680<br>18.7 | 43.6<br>72.4<br>119<br>2.36 | 0.03<br>0.03<br>0.07<br>0.13 |

As shown by the data in Table 2, for the first tested compound, brain to plasma ratios ranged from 0.14-0.46, representing significant brain penetration. Minimal to no penetration into the CNS was observed with the second tested compound, which had brain to plasma ratios ranging from 0.03 to 0.13. This latter compound is a peripherally selective analogue of otenabant. Compounds that are both potent against CB1 and have a high degree of selectivity have been identified. These compounds have high TPSA but do not possess the potential for intramolecular H-bonding to increase their penetration into the CNS.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound according to the structure:

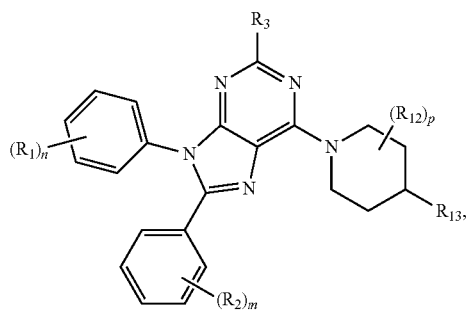

wherein $R_1$ and $R_2$ are halo substituents;
m and n are each independently integers from 0 to 5;
p is 0;
$R_3$ is H;
$R_{13}$ is selected from the group consisting of:
  $NR_6SO_2R_9$, wherein $R_9$ is selected from C1-10 alkyl and halo-substituted C1-10 alkyl;
  $NR_6CONR_7R_{11}$, wherein $R_7$ is selected from C-10 alkyl and H and wherein $R_{11}$ is selected from C1-10 alkyl, C1-10 alkoxy-substituted C1-10 alkyl, and halo-substituted C1-10 alkyl;
  $NR_6COR_{15}$, wherein $R_{15}$ is selected from: C1-12 alkyl; halo-substituted C1-12 alkyl; C1-12 heteroalkyl in the form of an alkyl group having at least one sulfur, oxygen, or nitrogen atom within the chain; phenyl; alkyl-substituted phenyl; and halo-substituted phenyl; and
  $NR_6CO_2R_7$, wherein $R_7$ is selected from C1-10 alkyl and C1-10 alkoxy-substituted C1-10 alkyl; and
$R_6$ is H;
or a pharmaceutically acceptable salt or stereoisomer thereof.

2. The compound of claim 1, wherein $R_1$ and $R_2$ are Cl.
3. The compound of claim 1, wherein m and n are each 1.
4. The compound of claim 2, wherein m and n are each 1.
5. The compound of claim 1, wherein n is 1 and the $R_1$ substituent is at the para position and m is 1 and the $R_2$ substituent is at the ortho position.
6. The compound of claim 5, wherein $R_1$ and $R_2$ are Cl.
7. The compound of claim 1, wherein $R_{13}$ is $NR_6COR_{15}$ and $R_{15}$ is a C1-12 alkyl comprising one or more cycloalkyl rings.
8. The compound of claim 2, wherein $R_{13}$ is $NR_6COR_{15}$ and $R_{15}$ is a C1-12 alkyl selected from isobutyl, n-butyl, cyclopentyl, cyclopentylmethyl, cyclohexyl, and cyclohexylmethyl.
9. The compound of claim 1, wherein $R_{13}$ is $NR_6COR_{15}$ and $R_{15}$ is a halo-substituted C1-12 alkyl, and wherein the halo is F.

10. The compound of claim 1, wherein $R_{13}$ is $NR_6COR_{15}$ and $R_{15}$ is a C1-12 heteroalkyl comprising at least one S atom.

11. The compound of claim 10, wherein $R_{13}$ is $NR_6COR_{15}$ and $R_{15}$ is a cyclic C1-12 heteroalkyl.

12. The compound of claim 1, wherein $R_{13}$ is $NR_6COR_{15}$ and $R_{15}$ is a halo-substituted phenyl, and wherein the halo is F.

13. The compound of claim 1, wherein $R_{13}$ is $NR_6SO_2R_9$ and $R_9$ is $CH_3$.

14. The compound of claim 1, wherein $R_{13}$ is $NR_6SO_2R_9$ and $R_9$ is a halo-substituted C1-10 alkyl, and wherein the halo is F.

15. The compound of claim 1, wherein $R_{13}$ is $NR_6SO_2R_9$ and $R_9$ is a cyclic C1-10 alkyl.

16. The compound of claim 1, wherein $R_{13}$ is $NR_6CO_2R_7$ and $R_7$ is a cyclic C1-10 alkyl.

17. The compound of claim 1, wherein $R_{13}$ is $NR_6CONR_7R_{11}$ and $R_{11}$ is a C1-10 alkyl selected from the group consisting of ethyl, propyl, and butyl.

18. The compound of claim 17, wherein $R_{11}$ is selected from n-propyl, isopropyl, n-butyl, sec-butyl, isobutyl, and t-butyl.

19. The compound of claim 1, wherein $R_{13}$ is $NR_6CONR_7R_{11}$ and $R_{11}$ is a C1-10 alkyl comprising one or more cycloalkyl groups.

20. The compound of claim 1, wherein $R_{13}$ is $NR_6CONR_7R_{11}$ and halo-substituted C1-10 alkyl, and wherein the halo is F.

* * * * *

UNITED STATES PATENT AND TRADEMARK OFFICE
CERTIFICATE OF CORRECTION

| | | |
|---|---|---|
| PATENT NO. | : 9,458,160 B2 | |
| APPLICATION NO. | : 14/922583 | |
| DATED | : October 4, 2016 | |
| INVENTOR(S) | : Rangan Maitra et al. | |

It is certified that error appears in the above-identified patent and that said Letters Patent is hereby corrected as shown below:

On the Title Page

Under the heading "Related U.S. Application Data," the filing date of the Provisional application no. 61/600,229 is incorrectly listed as February 15, 2013. The correct filing date is February 17, 2012.

In the Claims

In the text of Claim 17 which appears on Column 71, Line 19, there is a typographical error: $R_{il}$ should read as $R_{11}$.

In the text of Claim 19 which appears on Column 71, Line 25, there is a typographical error: $R_{il}$ should read as $R_{11}$.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*